US008664467B2

(12) United States Patent
Roe et al.

(10) Patent No.: US 8,664,467 B2
(45) Date of Patent: *Mar. 4, 2014

(54) ABSORBENT ARTICLES WITH FEEDBACK SIGNAL UPON URINATION

(75) Inventors: Donald Carroll Roe, West Chester, OH (US); Jennifer Joan Nandrea, Cincinnati, OH (US); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 797 days.

This patent is subject to a terminal disclaimer.

(21) Appl. No.: 11/724,713

(22) Filed: Mar. 16, 2007

(65) Prior Publication Data

US 2007/0287971 A1    Dec. 13, 2007

Related U.S. Application Data

(60) Provisional application No. 60/788,482, filed on Mar. 31, 2006.

(51) Int. Cl.
*A61F 13/20*    (2006.01)

(52) U.S. Cl.
USPC ........... 604/361; 604/358; 604/362; 128/886; 200/61.04; 200/61.05

(58) Field of Classification Search
USPC ........ 604/358, 361, 362; 128/886; 200/61.04, 200/61.05
See application file for complete search history.

(56) References Cited

U.S. PATENT DOCUMENTS

| | | | |
|---|---|---|---|
| 2,075,189 A | 3/1937 | Galligan et al. |
| 3,675,654 A | 7/1972 | Baker |
| 3,759,261 A | 9/1973 | Wang |
| 3,848,594 A | 11/1974 | Buell |
| 3,860,003 A | 1/1975 | Buell |
| 3,881,491 A | 5/1975 | Whyte |
| 3,911,173 A | 10/1975 | Sprague, Jr. |
| 3,921,232 A | 11/1975 | Whyte |
| 3,929,135 A | 12/1975 | Thompson |
| 4,020,153 A | 4/1977 | Rowsell et al. |
| 4,022,210 A | 5/1977 | Glassman |

(Continued)

FOREIGN PATENT DOCUMENTS

DE    G 93 17 680.5    4/1995
EP    454105 B1    11/1995

(Continued)

OTHER PUBLICATIONS

U.S. Appl. No. 11/351,745, filed Feb. 10, 2006, Donald Roe.

(Continued)

*Primary Examiner* — Tatyana Zalukaeva
*Assistant Examiner* — Ilya Treyger
(74) *Attorney, Agent, or Firm* — Charles R. Matson; Laura L. Whitmer

(57) ABSTRACT

Absorbent articles incorporating sensory element members are disclosed. The absorbent articles may be disposable pant like garments designed to assist urinary toilet training such as of young children. Upon urination by the wearer, the article produces a feedback response which is transmitted to the wearer by the sensory element member. Wetness based, temperature based and other feedback responses are disclosed. The feedback response should be immediate and unmistakable to the wearer and also be temporary and harmless.

45 Claims, 9 Drawing Sheets

(56) References Cited

U.S. PATENT DOCUMENTS

| | | | |
|---|---|---|---|
| 4,022,211 A | 5/1977 | Timmons |
| 4,032,661 A | 6/1977 | Rowsell et al. |
| 4,033,994 A | 7/1977 | Watson et al. |
| 4,034,109 A | 7/1977 | Rowsell et al. |
| 4,070,449 A | 1/1978 | Rowsell et al. |
| 4,070,496 A | 1/1978 | Rowsell et al. |
| 4,078,568 A | 3/1978 | Etes et al. |
| 4,089,765 A | 5/1978 | Dudley |
| 4,107,364 A | 8/1978 | Sisson |
| 4,140,115 A | 2/1979 | Schonfeld |
| 4,150,052 A | 4/1979 | Watson et al. |
| 4,153,679 A | 5/1979 | Rowsell et al. |
| 4,178,459 A | 12/1979 | Watson et al. |
| 4,192,311 A | 3/1980 | Felfoldi |
| 4,192,785 A | 3/1980 | Chen et al. |
| 4,193,936 A | 3/1980 | Watson et al. |
| 4,209,563 A | 6/1980 | Sisson |
| 4,226,988 A | 10/1980 | Watson et al. |
| 4,231,369 A | 11/1980 | Sorensen et al. |
| 4,231,370 A | 11/1980 | Mroz |
| 4,289,794 A | 9/1981 | Kleiner et al. |
| 4,296,093 A | 10/1981 | Rowsell et al. |
| 4,296,255 A | 10/1981 | Roswell et al. |
| 4,324,246 A | 4/1982 | Mullane et al. |
| 4,327,731 A | 5/1982 | Powell |
| 4,342,314 A | 8/1982 | Radel et al. |
| 4,393,080 A | 7/1983 | Pawelchak et al. |
| 4,459,425 A | 7/1984 | Amano et al. |
| 4,463,045 A | 7/1984 | Ahr et al. |
| 4,505,976 A | 3/1985 | Doehnert et al. |
| 4,507,121 A | 3/1985 | Leung |
| 4,515,595 A | 5/1985 | Kievit et al. |
| 4,551,490 A | 11/1985 | Doyle et al. |
| 4,573,986 A | 3/1986 | Minetola et al. |
| 4,585,450 A * | 4/1986 | Rosch et al. ............... 604/390 |
| 4,593,053 A | 6/1986 | Jevne et al. |
| 4,609,518 A | 9/1986 | Curro et al. |
| 4,609,587 A | 9/1986 | Giordano et al. |
| 4,610,678 A | 9/1986 | Weisman et al. |
| 4,629,643 A | 12/1986 | Curro et al. |
| 4,636,207 A * | 1/1987 | Buell ............... 604/370 |
| 4,662,875 A | 5/1987 | Hirotsu et al. |
| 4,663,220 A | 5/1987 | Wisneski et al. |
| 4,673,402 A | 6/1987 | Weisman et al. |
| 4,695,278 A | 9/1987 | Lawson |
| 4,699,146 A | 10/1987 | Sieverding |
| 4,699,622 A | 10/1987 | Toussant et al. |
| 4,705,513 A | 11/1987 | Sheldon |
| 4,710,189 A | 12/1987 | Lash |
| 4,720,415 A | 1/1988 | Vander Wielen et al. |
| 4,738,257 A | 4/1988 | Meyer et al. |
| 4,785,996 A | 11/1988 | Ziecker et al. |
| 4,795,454 A | 1/1989 | Dragoo |
| 4,808,178 A | 2/1989 | Aziz et al. |
| 4,816,025 A | 3/1989 | Foreman |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,963,140 A | 10/1990 | Robertson et al. |
| 4,965,122 A | 10/1990 | Morman |
| 4,968,312 A | 11/1990 | Khan |
| 4,981,747 A | 1/1991 | Morman |
| 4,990,147 A | 2/1991 | Freeland |
| 5,006,394 A | 4/1991 | Baird |
| 5,026,364 A | 6/1991 | Robertson |
| 5,037,416 A | 8/1991 | Allen et al. |
| 5,062,840 A | 11/1991 | Holt et al. |
| 5,064,421 A | 11/1991 | Tracy |
| 5,092,861 A | 3/1992 | Nomura et al. |
| 5,114,781 A | 5/1992 | Morman |
| 5,116,662 A | 5/1992 | Morman |
| 5,124,188 A | 6/1992 | Roe et al. |
| 5,133,707 A | 7/1992 | Rogers et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| D331,969 S | 12/1992 | Hunt |
| 5,167,653 A | 12/1992 | Igaue et al. |
| 5,167,655 A | 12/1992 | McCoy |
| 5,167,897 A | 12/1992 | Weber et al. |
| 5,171,236 A | 12/1992 | Dreier et al. |
| 5,178,139 A | 1/1993 | Angelillo et al. |
| D334,426 S | 3/1993 | Meis |
| 5,197,958 A | 3/1993 | Howell et al. |
| 5,221,274 A | 6/1993 | Buell et al. |
| 5,224,405 A | 7/1993 | Pohjola |
| 5,226,992 A | 7/1993 | Morman |
| 5,246,432 A | 9/1993 | Suzuki et al. |
| 5,246,433 A | 9/1993 | Hasse et al. |
| D341,197 S | 11/1993 | Patterson |
| 5,260,345 A | 11/1993 | Desmarais et al. |
| 5,266,592 A | 11/1993 | Grub et al. |
| 5,266,928 A * | 11/1993 | Johnson ............... 340/604 |
| 5,269,775 A | 12/1993 | Freeland et al. |
| 5,306,266 A | 4/1994 | Freeland |
| 5,318,555 A | 6/1994 | Siebers et al. |
| 5,330,458 A | 7/1994 | Buell et al. |
| 5,330,459 A | 7/1994 | Lavon et al. |
| 5,336,545 A | 8/1994 | Morman |
| 5,342,338 A | 8/1994 | Roe |
| 5,342,343 A | 8/1994 | Kitaoka et al. |
| 5,348,750 A | 9/1994 | Greenberg |
| 5,358,500 A | 10/1994 | Lavon et al. |
| 5,359,525 A | 10/1994 | Weyenberg |
| 5,380,313 A | 1/1995 | Goulait et al. |
| 5,387,207 A | 2/1995 | Dyer et al. |
| 5,397,316 A | 3/1995 | Lavon et al. |
| 5,397,318 A | 3/1995 | Dreier |
| 5,407,439 A | 4/1995 | Goulait |
| 5,425,726 A | 6/1995 | Shimizu et al. |
| 5,428,076 A | 6/1995 | Roe |
| 5,460,622 A | 10/1995 | Dragoo et al. |
| 5,468,236 A | 11/1995 | Everhart |
| 5,470,639 A | 11/1995 | Gessner et al. |
| 5,514,121 A | 5/1996 | Roe et al. |
| 5,518,801 A | 5/1996 | Chappell et al. |
| 5,540,671 A | 7/1996 | Dreier |
| 5,540,673 A | 7/1996 | Thomas et al. |
| 5,540,976 A | 7/1996 | Shawver et al. |
| 5,542,942 A | 8/1996 | Kline et al. |
| 5,554,142 A | 9/1996 | Dreier et al. |
| 5,554,143 A | 9/1996 | Roe et al. |
| 5,554,145 A | 9/1996 | Roe et al. |
| 5,567,609 A | 10/1996 | Sarras, Jr. et al. |
| 5,569,233 A | 10/1996 | Goulait |
| 5,569,234 A | 10/1996 | Buell et al. |
| 5,570,082 A * | 10/1996 | Mahgerefteh et al. ........ 340/604 |
| 5,571,096 A | 11/1996 | Dobrin et al. |
| 5,580,411 A | 12/1996 | Nease et al. |
| 5,607,760 A | 3/1997 | Roe |
| 5,608,119 A | 3/1997 | Amano et al. |
| 5,609,587 A | 3/1997 | Roe |
| 5,625,222 A | 4/1997 | Yoneda et al. |
| 5,635,191 A | 6/1997 | Roe et al. |
| 5,635,290 A | 6/1997 | Stopper et al. |
| 5,643,588 A | 7/1997 | Roe et al. |
| 5,649,914 A | 7/1997 | Glaug et al. |
| 5,653,703 A | 8/1997 | Roe et al. |
| 5,658,268 A | 8/1997 | Johns et al. |
| 5,659,538 A | 8/1997 | Stuebe et al. |
| 5,662,637 A | 9/1997 | Kitaoka et al. |
| 5,667,609 A | 9/1997 | Liu |
| 5,669,900 A | 9/1997 | Bullwinkel et al. |
| 5,681,298 A | 10/1997 | Brunner et al. |
| 5,702,376 A | 12/1997 | Glaug et al. |

(56) References Cited

U.S. PATENT DOCUMENTS

| | | | |
|---|---|---|---|
| H1732 H | 6/1998 | Johnson | |
| 5,766,212 A | 6/1998 | Jitoe | |
| 5,779,831 A | 7/1998 | Schmitz | |
| 5,790,035 A * | 8/1998 | Ho | 340/573.5 |
| 5,797,892 A | 8/1998 | Glaug et al. | |
| 5,851,204 A | 12/1998 | Mizutani et al. | |
| 5,865,823 A | 2/1999 | Curro | |
| 5,883,028 A | 3/1999 | Morman et al. | |
| 5,885,264 A | 3/1999 | Matsushita | |
| 5,891,124 A | 4/1999 | Nomura et al. | |
| 5,897,545 A | 4/1999 | Kline et al. | |
| 5,938,648 A | 8/1999 | Lavon et al. | |
| 5,941,864 A | 8/1999 | Roe | |
| 5,947,947 A | 9/1999 | Tanzer et al. | |
| 5,957,908 A | 9/1999 | Kline et al. | |
| 5,959,535 A * | 9/1999 | Remsburg | 340/604 |
| 5,968,025 A | 10/1999 | Roe et al. | |
| 5,977,430 A | 11/1999 | Roe et al. | |
| 5,980,087 A | 11/1999 | Brandon et al. | |
| 5,989,380 A | 11/1999 | Frischer | |
| 5,997,520 A | 12/1999 | Ahr et al. | |
| 5,997,989 A | 12/1999 | Gessner et al. | |
| 6,001,460 A | 12/1999 | Morman et al. | |
| 6,004,306 A | 12/1999 | Robles et al. | |
| 6,010,490 A | 1/2000 | Freeland et al. | |
| 6,013,063 A | 1/2000 | Roe et al. | |
| 6,015,764 A | 1/2000 | Mccormack et al. | |
| 6,017,537 A | 1/2000 | Alexander et al. | |
| 6,045,543 A | 4/2000 | Pozniak et al. | |
| 6,075,178 A | 6/2000 | La Wilhelm | |
| 6,096,668 A | 8/2000 | Abuto et al. | |
| 6,103,647 A | 8/2000 | Shultz et al. | |
| 6,107,535 A | 8/2000 | Rossini et al. | |
| 6,107,537 A | 8/2000 | Elder et al. | |
| 6,114,597 A | 9/2000 | Romare | |
| 6,118,041 A | 9/2000 | Roe et al. | |
| 6,120,487 A | 9/2000 | Ashton | |
| 6,120,488 A | 9/2000 | Vanrijswijck et al. | |
| 6,120,489 A | 9/2000 | Johnson et al. | |
| 6,120,783 A | 9/2000 | Roe et al. | |
| 6,123,694 A | 9/2000 | Pieniak et al. | |
| 6,146,367 A | 11/2000 | Otsubo et al. | |
| 6,153,209 A | 11/2000 | Vega et al. | |
| 6,156,024 A | 12/2000 | Schulte et al. | |
| 6,156,424 A | 12/2000 | Taylor | |
| 6,166,285 A * | 12/2000 | Schulte et al. | 604/364 |
| 6,168,584 B1 | 1/2001 | Allen et al. | |
| 6,169,225 B1 | 1/2001 | Otsubo | |
| 6,186,991 B1 | 2/2001 | Roe et al. | |
| 6,214,788 B1 | 4/2001 | Velazco et al. | |
| 6,224,699 B1 | 5/2001 | Bett et al. | |
| 6,225,243 B1 | 5/2001 | Austin | |
| 6,229,063 B1 | 5/2001 | Shimoe et al. | |
| 6,253,159 B1 | 6/2001 | Bett et al. | |
| 6,264,641 B1 | 7/2001 | Van Gompel et al. | |
| 6,266,436 B1 | 7/2001 | Bett et al. | |
| 6,267,974 B1 | 7/2001 | Suares et al. | |
| 6,297,424 B1 | 10/2001 | Olson et al. | |
| 6,297,434 B1 | 10/2001 | Martello | |
| 6,307,119 B1 | 10/2001 | Cammarota et al. | |
| 6,313,372 B1 | 11/2001 | Suzuki | |
| 6,320,096 B1 | 11/2001 | Inoue et al. | |
| 6,328,982 B1 | 12/2001 | Shiroyama et al. | |
| 6,359,168 B1 | 3/2002 | Frerot et al. | |
| 6,384,728 B1 * | 5/2002 | Kanor et al. | 340/573.1 |
| 6,428,526 B1 | 8/2002 | Heindel et al. | |
| 6,429,526 B1 | 8/2002 | Blalock et al. | |
| 6,432,098 B1 | 8/2002 | Kline et al. | |
| 6,443,940 B1 | 9/2002 | Ashton et al. | |
| 6,444,064 B1 | 9/2002 | Henry et al. | |
| 6,448,467 B1 | 9/2002 | Herrlein et al. | |
| 6,465,073 B1 | 10/2002 | Morman et al. | |
| 6,478,786 B1 | 11/2002 | Glaug et al. | |
| 6,479,154 B1 | 11/2002 | Walton et al. | |
| 6,482,191 B1 | 11/2002 | Roe et al. | |
| 6,503,236 B1 | 1/2003 | Uitenbroek et al. | |
| 6,548,431 B1 | 4/2003 | Bansal et al. | |
| 6,548,432 B1 | 4/2003 | Hisada et al. | |
| 6,576,810 B1 | 6/2003 | Underhill et al. | |
| 6,579,274 B1 | 6/2003 | Morman et al. | |
| 6,583,722 B2 | 6/2003 | Jeutter et al. | |
| 6,590,136 B1 | 7/2003 | Young et al. | |
| 6,592,884 B2 | 7/2003 | Hofmann et al. | |
| 6,596,918 B1 | 7/2003 | Wehrle | |
| 6,617,016 B2 | 9/2003 | Zhang et al. | |
| 6,623,465 B1 | 9/2003 | Roe et al. | |
| 6,623,837 B2 | 9/2003 | Morman et al. | |
| 6,627,564 B1 | 9/2003 | Morman et al. | |
| 6,627,786 B2 * | 9/2003 | Roe et al. | 604/361 |
| 6,635,797 B2 * | 10/2003 | Olson et al. | 604/361 |
| 6,642,427 B2 | 11/2003 | Roe et al. | |
| 6,648,869 B1 | 11/2003 | Gillies et al. | |
| 6,657,100 B1 | 12/2003 | Underhill et al. | |
| 6,676,646 B2 | 1/2004 | Bast et al. | |
| 6,680,265 B1 | 1/2004 | Smith et al. | |
| 6,680,422 B2 | 1/2004 | Roe | |
| 6,692,475 B2 | 2/2004 | Mishima | |
| 6,702,795 B2 | 3/2004 | Klemp | |
| 6,710,221 B1 | 3/2004 | Pierce et al. | |
| 6,716,441 B1 | 4/2004 | Osborne et al. | |
| 6,719,742 B1 | 4/2004 | Mccormack et al. | |
| 6,726,668 B2 | 4/2004 | Underhill et al. | |
| 6,727,404 B2 | 4/2004 | Ruman et al. | |
| 6,733,483 B2 | 5/2004 | Raufman et al. | |
| 6,743,314 B2 | 6/2004 | Henry et al. | |
| 6,766,817 B2 | 7/2004 | da Silva | |
| 6,770,064 B1 | 8/2004 | Ruscher | |
| 6,772,708 B2 | 8/2004 | Klofta | |
| 6,811,865 B2 | 11/2004 | Morman et al. | |
| 6,849,324 B2 | 2/2005 | Meece et al. | |
| 6,870,479 B2 * | 3/2005 | Gabriel | 340/604 |
| 6,875,710 B2 | 4/2005 | Eaton et al. | |
| 6,881,206 B2 | 4/2005 | Underhill et al. | |
| 6,884,906 B2 | 4/2005 | Dewis et al. | |
| 6,904,865 B2 | 6/2005 | Klofta et al. | |
| 6,905,488 B2 | 6/2005 | Olson | |
| 6,909,028 B1 | 6/2005 | Shawver et al. | |
| 6,918,404 B2 | 7/2005 | da Silva | |
| 6,929,819 B2 | 8/2005 | Underhill et al. | |
| 6,942,894 B2 | 9/2005 | Alberg et al. | |
| 6,943,894 B2 | 9/2005 | Kitahara | |
| 6,955,733 B2 | 10/2005 | Miller et al. | |
| 6,957,160 B2 | 10/2005 | Miller et al. | |
| 6,958,432 B2 | 10/2005 | Underhill et al. | |
| 6,960,834 B2 | 11/2005 | Nakamura et al. | |
| 7,002,055 B2 | 2/2006 | Long et al. | |
| 7,033,341 B2 | 4/2006 | Mishima | |
| 7,056,411 B2 | 6/2006 | Desai et al. | |
| 7,066,586 B2 | 6/2006 | da Silva | |
| 7,123,981 B2 | 10/2006 | Dollevoet et al. | |
| 7,169,137 B2 | 1/2007 | Shimada | |
| 7,195,729 B2 | 3/2007 | Jackson et al. | |
| 7,223,818 B2 | 5/2007 | Autran et al. | |
| 7,285,255 B2 | 10/2007 | Kadlec et al. | |
| 7,301,036 B2 | 11/2007 | Parmee et al. | |
| 2002/0062117 A1 | 5/2002 | Raufman et al. | |
| 2002/0111596 A1 | 8/2002 | Fletcher et al. | |
| 2002/0138062 A1 | 9/2002 | Kuen et al. | |
| 2003/0028165 A1 | 2/2003 | Curro et al. | |
| 2003/0060794 A1 | 3/2003 | Olson | |
| 2003/0065298 A1 | 4/2003 | Krishnaswamy-Mirle et al. | |
| 2003/0073966 A1 | 4/2003 | Sosalla | |
| 2003/0077430 A1 | 4/2003 | Grimm et al. | |
| 2003/0087059 A1 | 5/2003 | Jackson et al. | |
| 2003/0088220 A1 | 5/2003 | Molander et al. | |
| 2003/0091807 A1 | 5/2003 | Desai et al. | |
| 2003/0114807 A1 | 6/2003 | Underhill et al. | |
| 2003/0114821 A1 | 6/2003 | Underhill et al. | |
| 2003/0120240 A1 | 6/2003 | Buell et al. | |
| 2003/0125682 A1 | 7/2003 | Olson et al. | |
| 2003/0125689 A1 | 7/2003 | Olson et al. | |
| 2003/0145937 A1 | 8/2003 | Underhill et al. | |
| 2003/0158532 A1 | 8/2003 | Magee et al. | |
| 2003/0158534 A1 | 8/2003 | Niki et al. | |

(56) References Cited

U.S. PATENT DOCUMENTS

| | | |
|---|---|---|
| 2003/0162458 A1 | 8/2003 | Tsujiyama et al. |
| 2003/0167049 A1 | 9/2003 | Gibbs |
| 2003/0193113 A1 | 10/2003 | Glovatsky |
| 2003/0199845 A1 | 10/2003 | Roe et al. |
| 2003/0233082 A1 | 12/2003 | Kline et al. |
| 2004/0030310 A1 | 2/2004 | Roe et al. |
| 2004/0064113 A1 | 4/2004 | Erdman |
| 2004/0067970 A1 | 4/2004 | Foster et al. |
| 2004/0071780 A1 | 4/2004 | Lillard et al. |
| 2004/0081680 A1 | 4/2004 | Pesce et al. |
| 2004/0082654 A1 | 4/2004 | Pesce et al. |
| 2004/0092902 A1 | 5/2004 | Hoffman et al. |
| 2004/0110442 A1 | 6/2004 | Rhim et al. |
| 2004/0127876 A1 | 7/2004 | Stevens |
| 2004/0132374 A1 | 7/2004 | Kobayashi |
| 2004/0162536 A1 | 8/2004 | Becker et al. |
| 2004/0167486 A1 | 8/2004 | Busam et al. |
| 2004/0191118 A1 | 9/2004 | Mody |
| 2004/0191279 A1 | 9/2004 | Klofta |
| 2004/0193113 A1 | 9/2004 | Gillis et al. |
| 2004/0193133 A1 | 9/2004 | Desai et al. |
| 2004/0211696 A1 | 10/2004 | Underhill et al. |
| 2004/0220540 A1 | 11/2004 | Underhill et al. |
| 2004/0254549 A1 | 12/2004 | Olson et al. |
| 2004/0254550 A1 | 12/2004 | Huang et al. |
| 2005/0027274 A1 | 2/2005 | Suzuki et al. |
| 2005/0049553 A1 | 3/2005 | Triplett et al. |
| 2005/0049568 A1 | 3/2005 | Underhill et al. |
| 2005/0065489 A1 | 3/2005 | Driskell et al. |
| 2005/0096612 A1 | 5/2005 | Davis et al. |
| 2005/0096618 A1 | 5/2005 | Magee et al. |
| 2005/0106980 A1 | 5/2005 | Abed et al. |
| 2005/0124952 A1 | 6/2005 | Zehner et al. |
| 2005/0125877 A1 | 6/2005 | Benjamin et al. |
| 2005/0125923 A1 | 6/2005 | Benjamin et al. |
| 2005/0129743 A1 | 6/2005 | Benjamin et al. |
| 2005/0139713 A1 | 6/2005 | Weber et al. |
| 2005/0147785 A1 | 7/2005 | Ahn et al. |
| 2005/0177123 A1 | 8/2005 | Catalan |
| 2005/0214461 A1 | 9/2005 | Desai et al. |
| 2005/0222546 A1 | 10/2005 | Vargo et al. |
| 2005/0228349 A1 | 10/2005 | Long et al. |
| 2005/0273071 A1 | 12/2005 | McKiernan et al. |
| 2006/0004333 A1 | 1/2006 | Olson |
| 2006/0025737 A1 | 2/2006 | Song et al. |
| 2006/0068168 A1 | 3/2006 | Olson et al. |
| 2006/0069361 A1 | 3/2006 | Olson et al. |
| 2006/0069362 A1 | 3/2006 | Odorzynski et al. |
| 2006/0111686 A1 | 5/2006 | Schneider |
| 2006/0212010 A1 | 9/2006 | Roe |
| 2006/0212018 A1 | 9/2006 | Roe |
| 2006/0224132 A1 | 10/2006 | Roe et al. |
| 2006/0247594 A1 | 11/2006 | Nickel et al. |
| 2006/0264858 A1 | 11/2006 | Roe et al. |
| 2007/0032766 A1 | 2/2007 | Liu |
| 2007/0049884 A1 | 3/2007 | Long et al. |
| 2007/0073261 A1 | 3/2007 | Ashton et al. |
| 2007/0287348 A1 | 12/2007 | Autran et al. |
| 2007/0287982 A1 | 12/2007 | Lodge et al. |
| 2007/0287983 A1 | 12/2007 | Lodge et al. |

FOREIGN PATENT DOCUMENTS

| | | |
|---|---|---|
| EP | 547497 | 6/1997 |
| EP | 0 937 446 A2 | 8/1999 |
| EP | 0 776 645 B1 | 3/2002 |
| EP | 1 216 673 A1 | 6/2002 |
| EP | 1 222 907 A2 | 7/2002 |
| EP | 1 287 799 A2 | 3/2003 |
| EP | 1 356 798 A1 | 10/2003 |
| EP | 1 279 357 B1 | 9/2005 |
| JP | 2004 141640 A | 5/2004 |
| WO | WO-94/14395 A1 | 7/1994 |
| WO | WO-95/16746 | 6/1995 |
| WO | WO-95 16746 A1 | 6/1995 |
| WO | WO 99/20216 A1 | 4/1999 |
| WO | WO 99/22688 A1 | 5/1999 |
| WO | WO 00/00233 A1 | 1/2000 |
| WO | WO 00/15169 A1 | 3/2000 |
| WO | WO 00/35401 A1 | 6/2000 |
| WO | WO 00/37006 A1 | 6/2000 |
| WO | WO 01/21126 A1 | 3/2001 |
| WO | WO 01/41691 A1 | 6/2001 |
| WO | WO 01/95845 A1 | 12/2001 |
| WO | WO 02/49564 A1 | 6/2002 |
| WO | WO-02/091968 A2 | 11/2002 |
| WO | WO 2004/026206 A1 | 4/2004 |
| WO | WO 2004/028403 A2 | 4/2004 |
| WO | WO-2004/071780 A2 | 8/2004 |
| WO | WO 2005/037159 A | 4/2005 |
| WO | WO-2005/041834 A1 | 5/2005 |
| WO | WO-2005/102239 A1 | 11/2005 |
| WO | WO-2006 017518 A2 | 2/2006 |
| WO | WO 2006/017674 A1 | 2/2006 |
| WO | WO 2006/028911 A1 | 3/2006 |
| WO | WO 2006/127519 A2 | 11/2006 |
| WO | WO 2007/017817 A3 | 7/2007 |

OTHER PUBLICATIONS

U.S. Appl. No. 11/724,709, Mar. 16, 2007, Donald Roe.
U.S. Appl. No. 11/724,851, Mar. 16, 2007, Donald Roe.
U.S. Appl. No. 11/724,922, Mar. 16, 2007, Donald Roe.
U.S. Appl. No. 11/724,838, Mar. 16, 2007, Donald Roe.
PCT Search Report mailed Aug. 23, 2006 (4 pages).
"Pampers Ultra Trainers" package, Size 3 from Finneytown Kroger's dated Oct. 3, 1998. 2 pages.
Timothy R. Schum, MD, et al.—Sequential Acquisition of Toilet-Training Skills: A Descriptive Study of Gender and Age Differences in Normal Children, *Pediatrics,* Mar. 2002, 7 pages vol. 109, No. 3.
International Search Report, mailed Oct. 7, 2007, PCT/US2006/009303, 11 pages (9939).
International Search Report, mailed Mar. 29, 2007, PCT/IB2006/052696, 10 pages (10097).
International Search Report, mailed Oct. 9, 2008, PCT/US2007/007171, 7 pages.
International Search Report, mailed Oct. 30, 2007, PCT/US2007/007171, 11 pages.
International Search Report, mailed Jun. 6, 2008, PCT/US2007/024933, 9 pages.
International Search Report, mailed Jul. 30, 2008, PCT/US2007/024933, 22 pages.
International Search Report, mailed Nov. 6, 2006, PCT/US2006/019580, 17 pages.

* cited by examiner

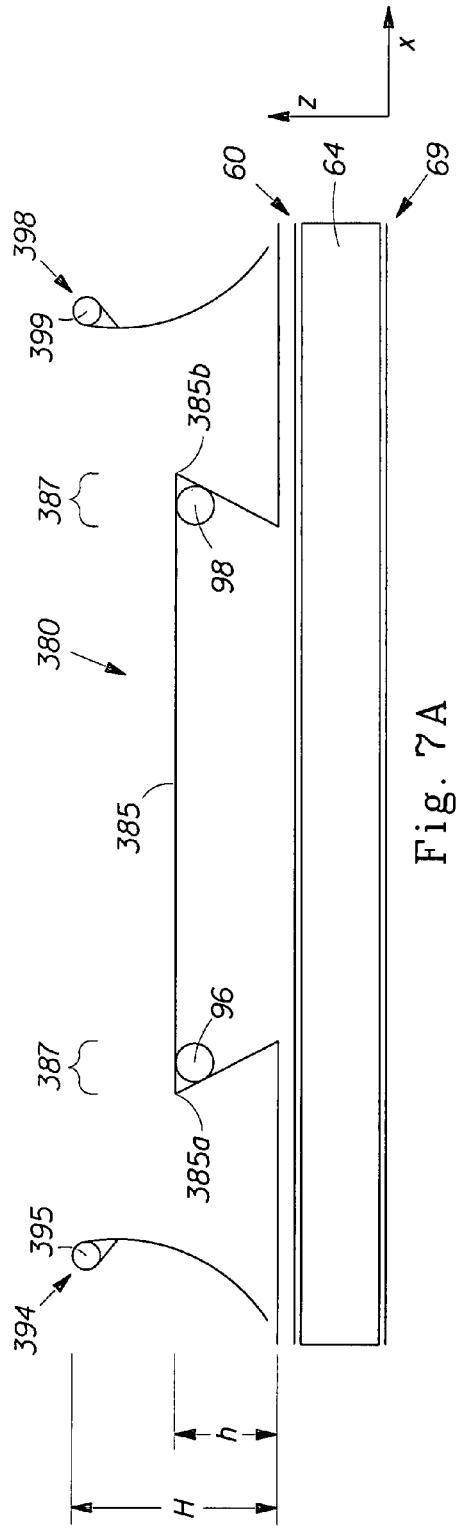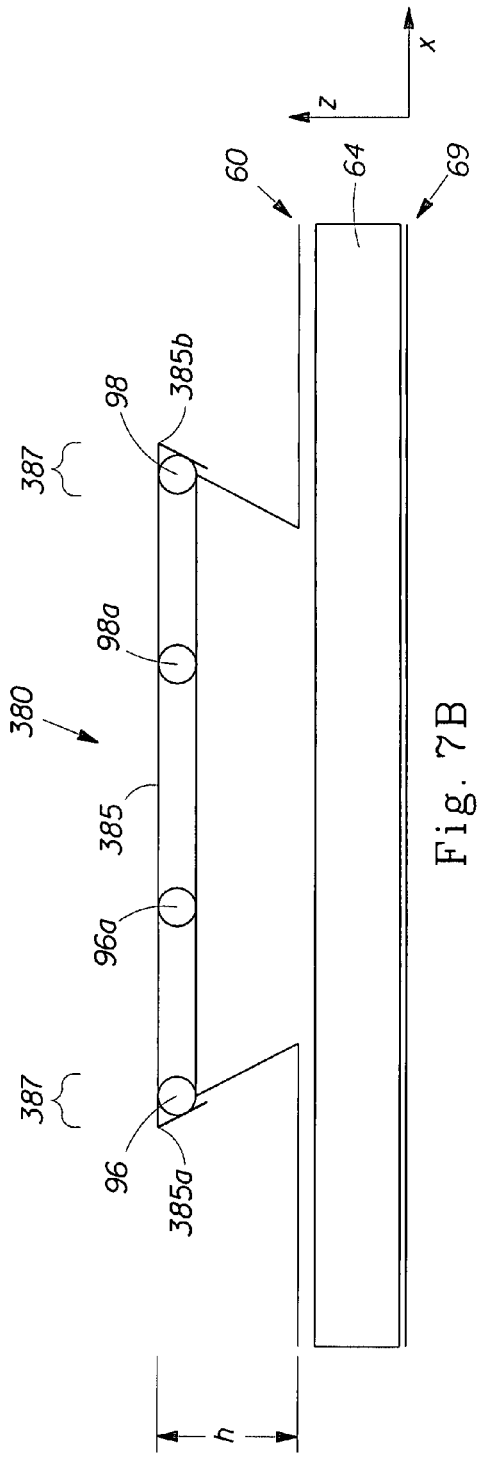
Fig. 7A
Fig. 7B

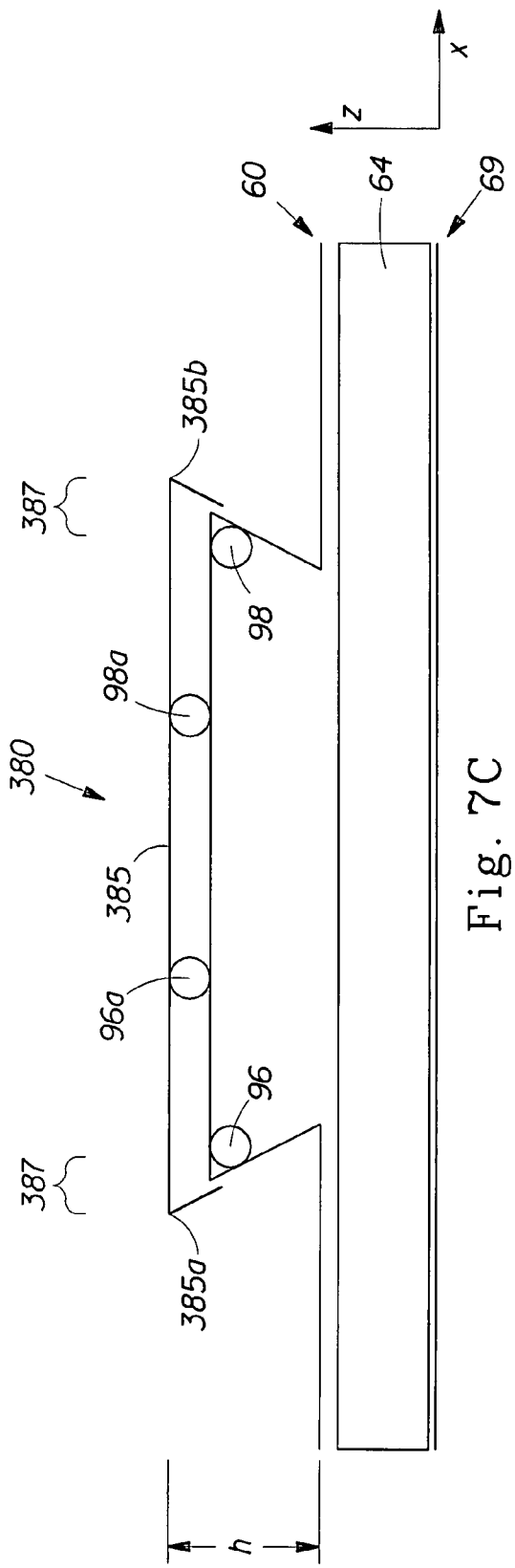
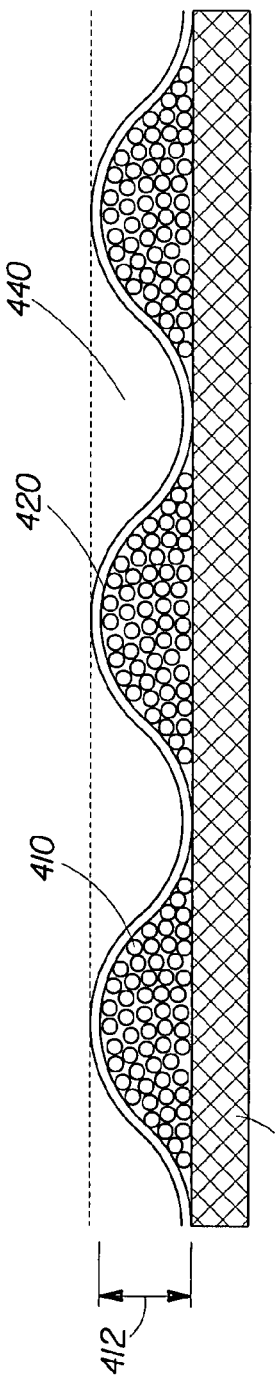

ABSORBENT ARTICLES WITH FEEDBACK SIGNAL UPON URINATION

CROSS REFERENCE TO RELATED APPLICATION

This application claims the benefit of U.S. Provisional Application No. 60/788,482, filed Mar. 31, 2006, the substance of which is incorporated herein by reference.

FIELD OF THE INVENTION

The present disclosure generally relates to absorbent articles, including diapers, training pants, pull-on diapers, inserts, diaper holders and liners, and the like, and in particular to an absorbent article with a feedback sensory element member, which may be adapted for use in urinary toilet training.

BACKGROUND OF THE INVENTION

Absorbent articles are well known in the art. These articles typically have an absorbent assembly held or positioned in proximity to the body of a wearer during use in order to capture and absorb bodily exudates discharged from the wearer. Typical absorbent articles include a topsheet facing the wearer, which permits fluid exudates to pass through, and an outer cover, which prevents the exudates from escaping from the absorbent article.

The toilet training stage may be referred to as the "point of exit" from the diaper product category because toddlers who have successfully completed toilet training typically no longer wear diapers. The age at which children are toilet trained in "developed" countries has increased steadily over the past several decades and is now in the range of about 24-48 months. One reason for which toilet training has become delayed is that significant technical improvements have been made in diaper dryness and comfort. For example, when wearing a typical modern diaper, the child may have dry skin even after one or more occurrences of urination. As a result, the child may feel little or no discomfort and often may not even be aware that he or she has urinated.

Some parents may have the child wear cotton training pants or cotton underwear during urinary training so the child feels discomfort following urination in his or her "pants." It is believed that such discomfort assists with learning or provides motivation to learn to voluntarily retain urine (at least until the child can urinate in a socially acceptable time/location). Cloth training pants leave the skin wet and, due to their high breathability, promote evaporative cooling of the skin, further enhancing discomfort. The current tradeoff in this approach, however, is that cloth training pants have poor urine containment, often leading to wet clothing and wet surroundings, e.g., carpeting, furniture, etc. There is a need to provide disposable absorbent articles where the article itself has features which facilitate toilet training without compromising the convenience of the disposable product form.

Several attempts have been made in the prior art to provide disposable absorbent articles which provide some sort of feedback such as a "coolness" or "wetness" signal to alert the wearer of the incidence of urination. Examples of such approaches have included garments which provide a "feel wet" signal. U.S. Pat. No. 6,958,432 discloses an example of a garment with a member which attempts to provide such a feeling of wetness. U.S. Pat. No. 6,642,427 discloses a garment which contains endothermic salts and similar substances to provide a temperature change or feeling of coolness. U.S. Pat. No. 5,797,892 discloses an article which attempts to change size or shape upon urination to provide a tactile feedback to the wearer upon urination.

These approaches found in the prior art have met with some commercial success and accomplish the training objective at least to some degree. It has been found during development of the present invention that several—sometimes contradictory—characteristics of feedback mechanisms are important. For example, it has been found during development of the present invention that an ideal feedback mechanism should provide a nearly immediate response upon urination. If the response time for the signal is too long, the child may not properly associate the signal with the urination event which triggered it. It has also been found during development of the present invention that the feedback mechanism should ideally also provide a temporary signal. The temporary duration of the signal helps to reinforce the association with the urination event. In other words, if the signal lasts too long or indefinitely the wearer may become undesirably accustomed to the signal. Additionally, a signal which persists may lead to undesirable impacts such as stress on the wearer's skin.

Another characteristic of well designed feedback mechanisms discovered during development of the present invention is that such mechanisms should be harmless to the wearer and the wearer's skin. For example, a feedback mechanism which provided prolonged contact of a urine saturated component with the skin could lead to skin irritation and, therefore, would not be ideal.

It has also been found during development of the present invention that ideal feedback mechanisms be unmistakable to the wearer. For example, if the signal provided to the wearer were too subtle or ambiguous the training benefit of the signal may not be effectively achieved.

Consequently, a need, therefore, exists for disposable absorbent articles and garments which provide urination feedback mechanisms which are as immediate and unmistakable to the wearer as possible. Such feedback mechanisms should also be temporary and harmless. It would desirable to provide an article that can facilitate urinary toilet training by enhancing a wearer's awareness that urination has occurred by providing such a signal to the wearer while at the same time providing the protection of an absorbent article to prevent soiling of the wearer's clothing and surroundings.

SUMMARY OF THE INVENTION

In one aspect of the invention an absorbent article for wearing about the lower torso of a wearer said absorbent article includes a first waist region, a second waist region disposed opposite the first waist region, and a crotch region connecting said first waist region and said second waist region. The article also includes an absorbent core disposed between the outer cover and the topsheet. Additionally, the article also includes a sensory element member at least partially disposed in the crotch region of said absorbent article. The sensory element member provides a feedback response to the wearer upon a urination event. This feedback response occurs within about 60 seconds of said urination event and persists no longer than about 10 minutes beyond said urination event. The sensory element member includes a body contacting portion having an area of at least about 25 $cm^2$.

The feedback response may occur within about 30 seconds of said urination event or within about 15 seconds of said urination event. The feedback response may persist no longer about 600 seconds, or about 300 seconds, or about 150 seconds. The area of the body contact portion may be at least about 50 cm², or at least about 100 cm², or at least about 200 cm².

The feedback response provided by said sensory element member may be selected from the group consisting of elements providing a wetness sensation, a temperature change sensation, a coolness sensation, and combinations thereof. The body contacting portion of the sensory element member may include a skin protecting feature selected from the group consisting of a pH buffer material, Zinc Oxide, enzyme inhibitors, skin care compositions and combinations thereof. The article may be a disposable diaper or a pant-like garment. Pant-like garment configurations may include a refastenable fastening member. Such refastenable fastening member may include an adhesive or cohesive based fastening system, a tab and slot type mechanical fastener or a hook and loop type mechanical fastener. A pant-like garment of the present invention may comprise an easy open feature.

The article may include active graphics including at least one disappearing graphic or at least one appearing graphic. The outer cover of the article may include at least a portion which is water impermeable, breathable, and water vapor permeable.

The article may also include a second sensory element member which provides an audible feedback response upon a urination event. The sensory element may be at least partially separable from said topsheet. The sensory element member may be elastically foreshortened along at least a portion of the length of the topsheet. The body contacting portion of the sensory element may be enhanced via a contact promoting agent. The article may include a pair of barrier cuffs wherein the sensory element member is associated with said barrier cuffs.

In another aspect of the invention, an absorbent article for wearing about the lower torso of a wearer said absorbent article includes a first waist region, a second waist region disposed opposite the first waist region, and a crotch region connecting said front waist region and said rear waist region. The article also includes an outer cover, a water-permeable topsheet attached to the outer cover and having a body-facing surface and an absorbent core disposed between the outer cover and the topsheet. The article includes a wetness sensation member at least partially disposed in the crotch region of the absorbent article. The wetness sensation member provides a wetness indication to the wearer upon a urination event. The wetness sensation member has a body contacting portion which has a first Moisture Density of at least about 2 mg/cm² at 60 seconds after the urination event and a second Moisture Density at 10 minutes after said urination event of less than about 80% of the first Moisture Density.

The first Moisture Density may be at least about 4 mg/cm² or at least about 5 gm/cm² at 60 seconds after said urination event. The second Moisture Density at 10 minutes after said urination event may be less than about 75% or less than about 70% of the first Moisture Density.

The absorbent article of may also include a temperature sensation member at least partially disposed in the crotch region of the absorbent article. Such temperature sensation member may provide a temperature change sensation to the wearer upon a urination event. The temperature change sensation may occur within about 30 seconds of the urination event and persist no longer than about 300 seconds beyond the urination event. The temperature change sensation member may provide a surface temperature change of from about 5° C. to about 20° C. at 30 seconds after the urination event.

The wetness sensation member may include body contacting portion having an area of at least about 25 cm² or of at least about 100 cm².

The article may be a disposable pant-like garment. Such a disposable pant like garment may include a refastenable fastening member or may include an easy open feature. The article may include active graphics disposed on at least a portion of the article. The outer cover may include a portion which is water impermeable, breathable and water vapor permeable.

In another aspect of the invention, an absorbent article for wearing about the lower torso of a wearer said absorbent article includes a front waist region, a rear waist region disposed opposite the front waist region, and a crotch region connecting the front waist region and the rear waist region. The article also includes an outer cover, a water-permeable topsheet attached to the outer cover and having a body-facing surface. The article includes an absorbent core disposed between the outer cover and the topsheet. The article also includes a temperature change member at least partially disposed in the crotch region of the absorbent article. The temperature change member provides a temperature change to the wearer upon a urination event. The temperature change occurs within about 30 seconds of the urination event and persists no longer than about 300 seconds beyond the urination event. The temperature change member provides a surface temperature change of from about 5° C. to about 20° C. at 30 seconds after the urination event.

The absorbent article may further include a wetness sensation member at least partially disposed in the crotch region of the absorbent article. The wetness sensation member may provide a wetness indication to the wearer upon a urination event. The wetness sensation member may have a body contacting portion which has a first Moisture Density of at least about 2 mg/cm² at 60 seconds after the urination event and a second Moisture Density at 10 minutes after the urination event of less than about 80% of said first Moisture Density.

The temperature change may occur within about 15 seconds or within about 10 seconds of the urination event. The temperature change may persist no longer than about 150 seconds. The temperature change member may include a body contacting portion having an area of at least about 25 cm or at least about 100 cm. The article may be a disposable pant-like garment. Such a disposable pant like garment may include a refastenable fastening member or an easy open feature. The article may include active graphics disposed on at least a portion of the article. The outer cover may include a portion which is water impermeable, breathable and water vapor permeable.

In another aspect of the invention an absorbent article for wearing about the lower torso of a wearer said absorbent article includes a front waist region, a rear waist region disposed opposite the front waist region, and a crotch region connecting the front waist region and the rear waist region. The article also includes an outer cover, a water-permeable topsheet attached to the outer cover and having a body-facing surface. The article includes an absorbent core disposed between the outer cover and the topsheet. The article also includes a temperature change member at least partially disposed in the crotch region of the absorbent article. The temperature change member provides a temperature change upon a urination event. The temperature change occurs: at a rate of at least about 1° C./sec within the first 2 minutes following the urination event.

The temperature change may occur at a rate of at least 2° C./sec within the first 20 seconds or within the first 5 seconds following the urination event. The temperature change may occur at a rate of at least 3° C./sec within the first 20 seconds or within the first 5 seconds following the urination event. The temperature change may occur at a rate of at least 5° C./sec within the first 20 seconds or within the first 5 seconds following the urination event.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIGS. 7a-7c are cross-sectional views of another embodiment of an absorbent article.

FIG. 8 is a cross-sectional view of a preferred embodiment of the absorbent core.

DETAILED DESCRIPTION OF THE INVENTION

Figure 1:
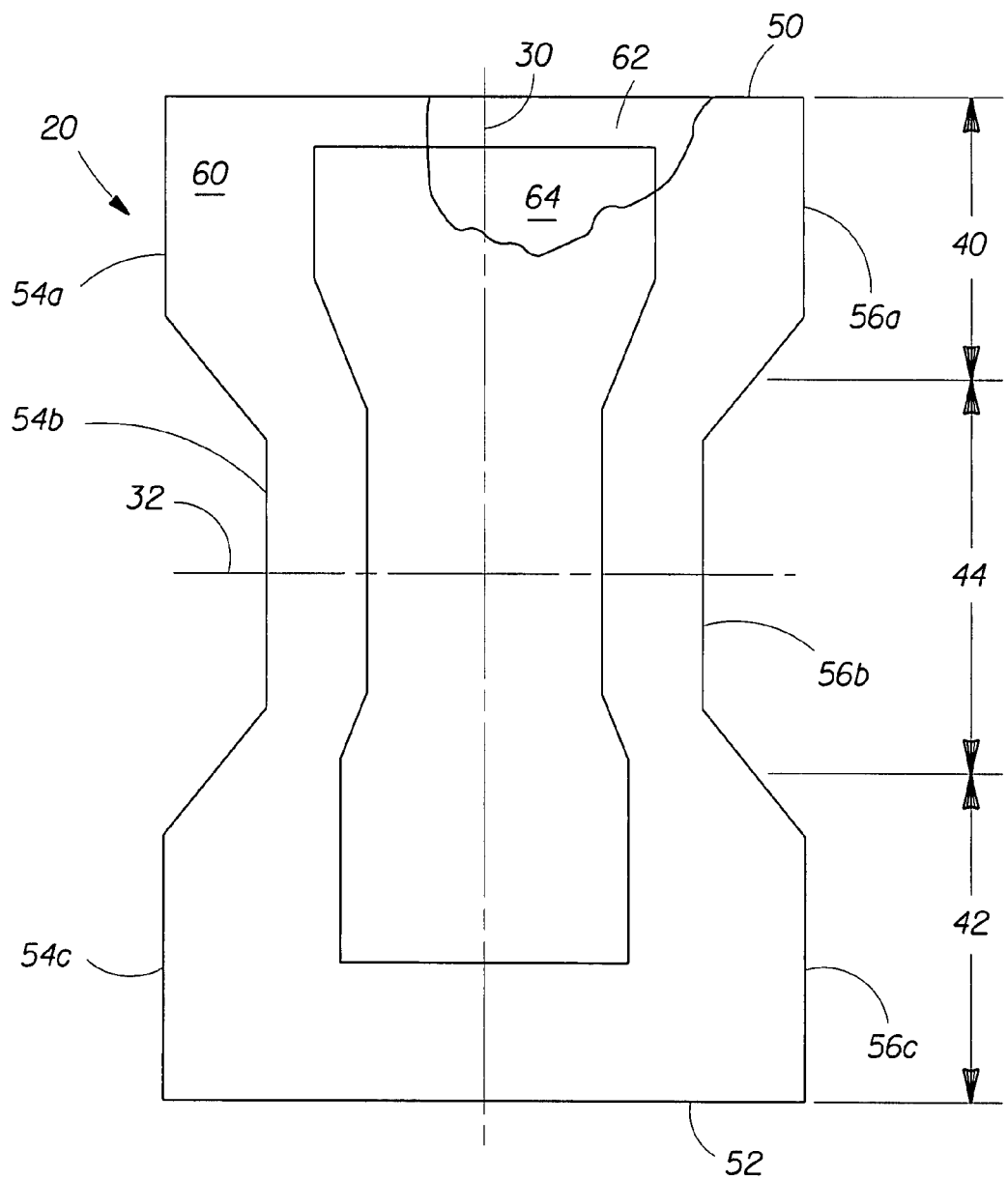
FIG. 1 is a plan view of an absorbent article with a section of a topsheet removed to expose an underlying absorbent core.

Definitions
As used herein, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "associated with", in relation to highlighting, refers at least to highlighting that is on an element or to highlighting that is disposed proximate to an element.

The term "associative correlation" refers to establishing a mutual or reciprocal relation between the visible highlighting and that with which it is being associatively correlated so that an association, i.e. a mental connection or bond, is formed between the two. This term is used in the context of associatively correlating the respective visible forms of the visible highlighting and an externally visible graphics in or on the absorbent article as well as in the context of associatively correlating the visible highlighting or graphics with the concept of urinary toilet training. For example, associatively correlated graphics may serve in concert to draw attention to an opportunity for urinary toilet training when an absorbent article is viewed prior to its being worn, to provide an externally visible reminder of the presence of the sensory element member in the interior of the absorbent article while it is being worn, etc. Similarly, visible highlighting that provides a visual reference to a topic related to urinary toilet training, such as dryness, wetness, or protection from wetness, may serve to associatively correlate the visible highlighting to the concept of urinary toilet training and thereby facilitate an opportunity for urinary toilet training.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "caregiver" refers to a person other than the child, such as, a parent, babysitter, family member, teacher, day care worker, or other person who is able to provide sufficient assistance to the child to complete a personal hygiene task.

The term "character image" refers to a graphic containing an anthropomorphic image, and in particular an image having or suggesting human form or appearance which ascribes human motivations, characteristics or behavior to inanimate objects, animals, natural phenomena, toys, cartoon characters, or the like. The character image may be associated with popular characters in the media, advertising or well known in a particular culture. Ideally they are characters that the user, particularly if a child, cares about and wants to identify with.

The term "coloration" refers to the arrangement or degree of coloring especially when used to visibly differentiate an object or a portion of an object in order to visibly highlight it.

The term "coloring" refers to the effect produced by applying or combining colors in and/or on an object or a portion of an object.

The term "diaper" refers to an absorbent article generally worn by infants, children, and/or incontinent persons about the lower torso and having the general form of a sheet, different portions of which are fastened together to encircle the waist and the legs of the wearer.

The term "disposable" refers to absorbent articles that generally are not intended to be laundered or otherwise restored or reused as absorbent articles, i.e., they are intended to be discarded after a single use and, preferably, to be recycled, composted or otherwise disposed of in an environmentally compatible manner.

The term "disposed" is used to mean that an element(s) is formed (joined and positioned) in a particular place or position as a unitary structure with other elements or as a separate element joined to another element.

The term "graphic" refers to a product of graphic art or a graphic representation in a pictorial form. A graphic may be a symbol, shape, image, text, or other form of indicia.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower" and "top" and "bottom", respectively.

The term "lateral" or "transverse" refers to a direction running at a 90 degree angle to the longitudinal direction and includes directions within ±45° of the lateral direction.

The term "longitudinal" refers to a direction running parallel to the maximum linear dimension of the article and includes directions within ±45° of the longitudinal direction.

The terms "pre-literate" and "incapable of reading" are used interchangeably herein to mean the inability of a child to correctly understand, comprehend and follow prompts written in a language that the child can speak without assistance of a caregiver. The ability of a child to recognize letters and/or read one or two isolated words still means that the child is "incapable of reading" since he or she is unable to understand, comprehend and follow such written prompts, without assistance. However, this definition of "incapable of reading" does not exclude the child from being able to understand, comprehend and follow visual prompts which are presented in the form of drawings, icons, symbols, gestures, cartoons and the like.

The term "refastenable" refers to the property of two elements being capable of releasable attachment, separation, and subsequent releasable reattachment without substantial permanent deformation or rupture.

The terms "releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

The term "solid coloring" refers to the unbroken, i.e., uninterrupted, coloring of an area as contrasted with the discrete line-like form of some graphics.

The term "toilet training" refers to the development of continence, which is the ability to voluntarily retain one's urine and feces. Individuals who are incontinent are unable to voluntarily retain their bodily discharges and, instead, urinate and defecate reflexively. For example, newborn babies are incontinent. Coincident with the development of continence, children typically develop the ability to voluntarily urinate and defecate, and cease reflexive elimination. This development of continence and of voluntary elimination, in place of reflexive elimination, may be accelerated and/or guided by caregivers through associative and conditioning techniques of training the child. For the purpose of the present disclosure, the term "toilet training" is used to denote training both for continence, itself, and for the voluntary elimination that is associated with continence. It is also noted that the term "toilet training" is synonymous with the term "potty training".

The terms "training pants," or "pant-like garments" refer to an absorbent article generally worn by infants and incontinent persons about the lower torso and having the general form of a pair of short pants that can be applied or removed from the wearer without unfastening.

The term "unitary" refers to an absorbent article that is formed of separate parts united together to form a coordinated entity so as to not require separate manipulative parts like a separate holder and liner.

The term "visible" refers to the quality of being capable of being seen by the naked eye under conditions of normal room lighting or in natural light during the daytime. Becoming "more visible" or "less visible" means changing in visibility to a noticeable extent when viewed under a generally constant or equal lighting condition.

The term "visible highlighting" refers to the visible differentiation of an object such that it noticeably stands out from its surroundings, e.g., by differing in coloration, hue, or tint, by differing in lightness, darkness, or contrast, by differing due to the presence or absence of graphical or solid color forms, or by any other variation serving to create noticeable visible differentiation.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or: simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The term "x-y plane" refers to the generally planar structure of a sheet material defined by its length and width and lies between the sheet material's two major surfaces regardless of whether or not the sheet material is flat or curved.

The term "z-direction" refers to the direction through the thickness of a sheet material and generally orthogonal to the x-y plane.

The term "sensory element member" is analogous to "sensation member" and "feedback response member" as used herein or in copending applications 60/788,482, 60/788,505, 60/788,343, 60/788,489, and 60/788,415 all filed on Mar. 31, 2006.

Description

FIG. 1 is a plan view of an exemplary disposable absorbent article 20 in its flat, uncontracted state, i.e., without elastic-induced contraction. Portions of the article 20 have been cut away to more clearly show the underlying structure of the disposable absorbent article 20. As illustrated, the portion of the disposable absorbent article 20 that contacts the wearer faces the viewer (i.e., showing the interior or inner side of the article). The disposable absorbent article 20 has a longitudinal axis 30 and a transverse axis 32.

One end portion of the disposable absorbent article 20 is configured as a first waist region 40 of the disposable absorbent article 20. The opposite end portion is configured as a second waist region 42 of the disposable absorbent article 20. The waist regions 40 and 42 generally comprise those portions of the disposable absorbent article 20 which, when worn, encircle the waist of the wearer. The waist regions 40 and 42 may include elastic elements such that they gather about the waist of the wearer to provide improved fit and containment. An intermediate portion of the disposable absorbent article 20 is configured as a crotch region 44, which extends longitudinally between the first and second waist regions 40 and 42. The crotch region 44 is that portion of the disposable absorbent article 20 which, when the disposable absorbent article 20 is worn, is generally positioned between the legs of the wearer.

The disposable absorbent article 20 has a laterally extending first waist edge 50 in the first waist region 40 and a longitudinally opposing and laterally extending second waist edge 52 in the second waist region 42. The disposable absorbent article 20 has a first side edge 54 and a laterally opposing second side edge 56, both side edges extending longitudinally between the first waist edge 50 and the second waist edge 52. The portion of the first side edge 54 in the first waist region 40 is designated 54a, the portion in the crotch region 44 is designated 54b, and the portion in the second waist region 42 is designated 54c. The corresponding portions of the second side edge 56 are designated 56a, 56b, and 56c, respectively.

The disposable absorbent article 20 preferably comprises a water-permeable topsheet 60, an at least partially water-impermeable outer cover 62, and an absorbent assembly or core 64, which may be disposed between the topsheet 60 and the outer cover 62 with the topsheet 60 attached to the outer cover 62. The topsheet 60 may be fully or partially elasticized or may be foreshortened so as to provide a void space between the topsheet 60 and the core 64. As explained below, a fully or partially elasticized topsheet 60 may also to tend to draw a sensory element member against the skin of the wearer. Exemplary structures including elasticized or foreshortened topsheets are described in greater detail in U.S. Pat. Nos. 4,892,536; 4,990,147; 5,037,416; and 5,269,775, among others.

Figure 2A:
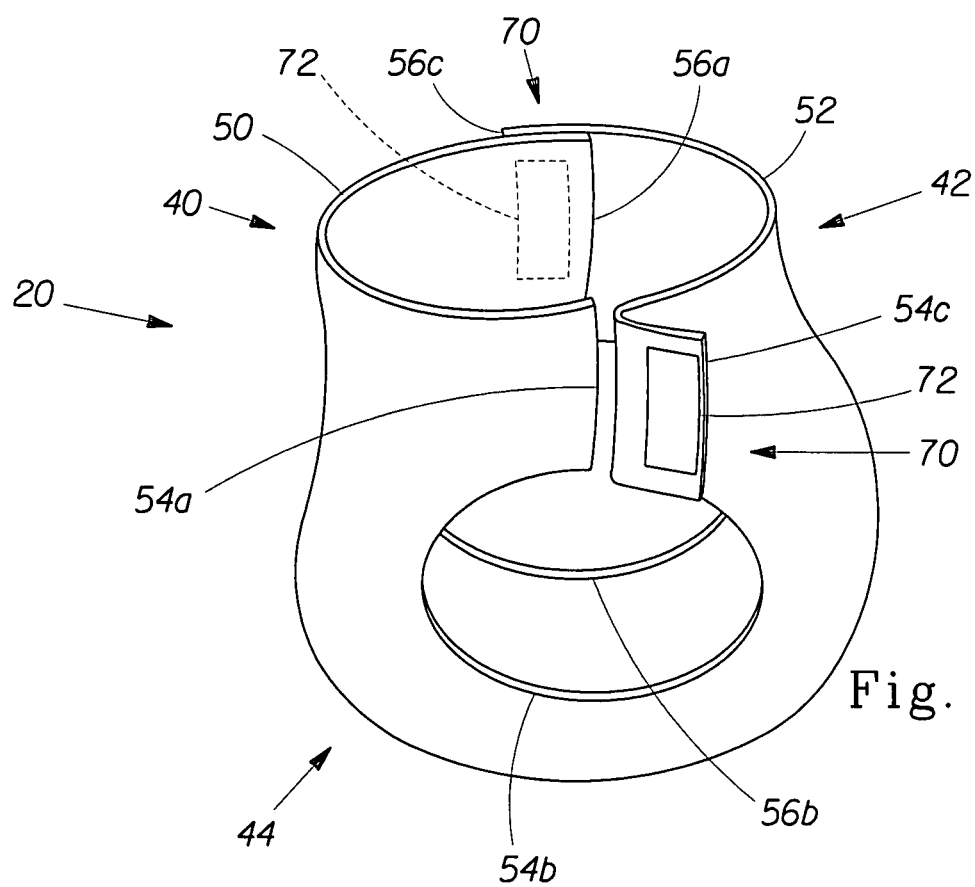
FIG. 2a is a perspective view of an exemplary absorbent article shown in its relaxed, contracted state, i.e., with the contraction induced by elastic members approximating its in use configuration.

FIG. 2a illustrates the article illustrated in FIG. 1 configured to as it would be worn. The disposable absorbent article 20 may be sealed at the sides so as to be configured as illustrated in FIG. 2a. However, the article 20 may instead include refastenable side seams 70 that can be used to fasten the waist regions 40, 42 together. According to one exemplary embodiment, the waist regions 40, 42 may be fastened at the sides to apply the article like a diaper. According to a further exemplary embodiment, illustrated in FIG. 2a, the side seams 70 may include fasteners 72 that can be used to configure the article like a pair of pull-on training pants or disposable pants.

As illustrated, the fasteners 72 may be disposed on the interior of the disposable absorbent article 20 in the second waist region 42 adjacent to the portion 54c of the first side edge 54 and adjacent to the portion 56c of the second side edge 56. The portion 54c of the side edge 54 is shown in an open condition, such as prior to closing and fastening or after being reopened. The portion 56c of the opposing side edge 56 is shown fastened, i.e., forming a pants configuration. In FIG. 2a, the second waist region 42 overlaps the first waist region 40 when they are fastened together.

The fasteners 72 may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive, cohesive, or selective adhesive material that releasably adheres to the mating surface.

Still other variations are also possible. For example, the fasteners 72 may be disposed on the interior of the article 20 in the first waist region 40 such that the first waist region 40 overlaps the second waist region 42 when they are fastened together. As another example, the fasteners 70 may be disposed on the exterior of the article 20 rather than on the interior. As a further example, the fasteners 70 may be used with a specific mating fastener surface particularly suited for cooperation with the fasteners 70 (e.g., a loop layer that works with a hook fastener, or a layer particularly treated to provide a suitable contacting surface for a specific adhesive). Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526, among others. Other fastener types may include "tab and slot" type mechanical refastenable fasteners. Buttons, snaps, zippers, and other types of fasteners, including refastenable fasteners are also possible.

It has been discovered during development of the present invention that the development of dressing and undressing skills as well as the development of continence are both related to and potentially important to a successful potty training experience. For example, a child may begin to recognize the urge to urinate and have an ability to control and delay the onset of urination. If such a child has a desire to use the toilet, but is wearing a disposable absorbent article which he or she :does not have the dexterity to remove readily, the child may not be able to use the toilet successfully. Therefore, it may be desirable to provide "easy open" features, such as those described further below either with or without refastenability features in a garment in combination with the sensory elements described herein to provide a garment having multiple potty training features in combination which synergistically re-enforce each other. Additionally, features which allow a child to more easily lower (or raise) the garment such as handles, printed indications of gripping features or the like such as those described in Co-pending application Ser. Nos. 11/083,606 and 11/083,607 and may also be included.

Figure 2B:
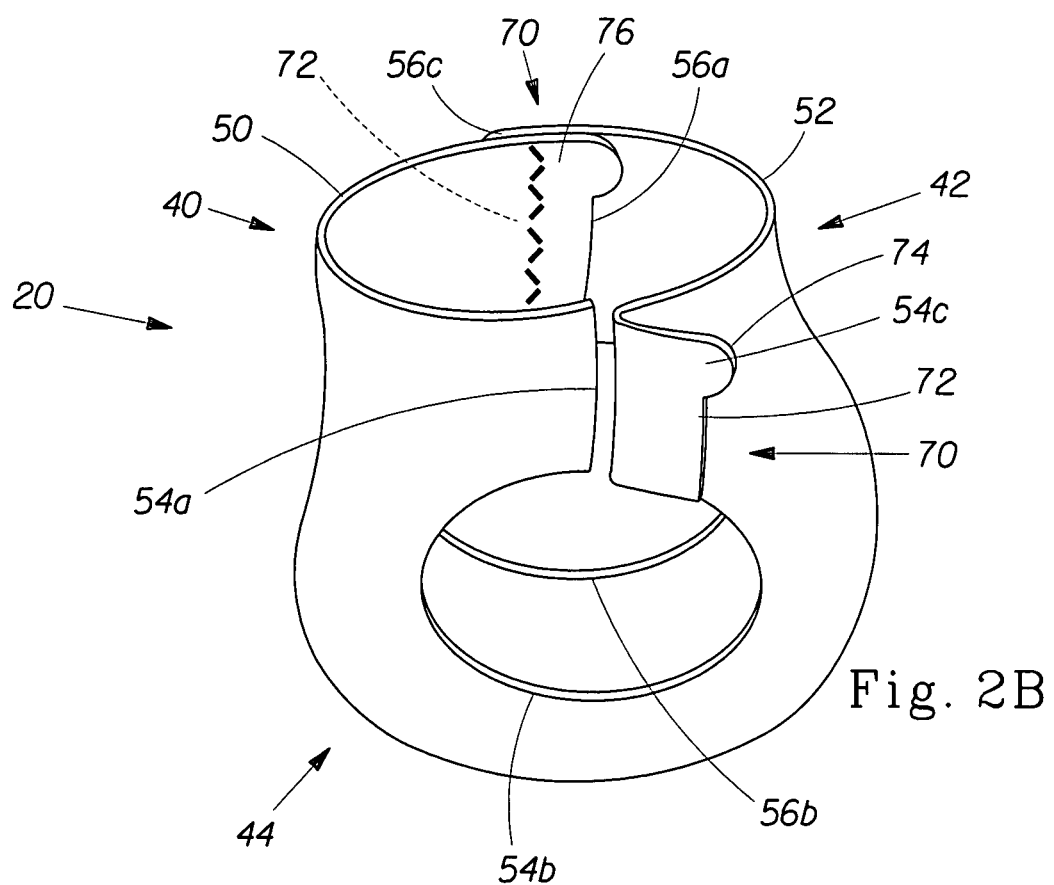
FIG. 2b is a perspective view similar to FIG. 2a showing an article having easy open side seam features.

The disposable absorbent article 20 may be provided with an easy open feature such as shown in FIG. 2b. Such an easy open feature can comprise a single element or a combination of elements designed to make the seams of the article easier to open so as to remove the article. For example the easy open feature could comprise a gripping tab 74. Additionally an easy open bond line pattern 76 could be provided either alone or in combination with the gripping tab 74. The easy open bond line pattern 76 shown in FIG. 2b can act as a type of "zipper" structure allowing propagation of an opening force along the side of the article 20. In some embodiments, the easy open bond line pattern may comprise indicia which indicate where to open the article. Such indicia are described in Co-pending application Ser. No. 11/198,614 filed on Aug. 5, 2005 in the name of Liu et al. Other easy open features could include a line of weakness, a notch or tab designed to propagate a tear, a tab gripping area or similar feature designed to allow for more easy release of a refastenable side fastener. Easy open features such as those described above can be provided if desired on articles having refastenable features or those which do not have refastenable fasteners—for example, a pant like garment with pre-formed side seams incorporating an easy open feature which can be used once, but which does not allow for refastenability once opened.

According to the present disclosure, the exemplary article 20, such as is illustrated in FIGS. 1 and 2a and 2b, may be combined with or assembled to include a sensory element member 80. Several embodiments, some with one or more variations, are illustrated in FIGS. 3a, 3b, 4a, 4b, 5a, 5b, 6a, and 6b. Elements common to all embodiments are numbered similarly in all Figures, while those elements unique to each embodiment are numbered differently, with the sensory element member according to a first embodiment being numbered as 80, a second embodiment as 180, and a third embodiment as 280. In addition, while the exemplary absorbent articles illustrated each include a single sensory element member, the articles may include a plurality of sensory element members either of the same type or of differing types according to other embodiments.

The sensory elements (incorporated into sensory element members) of the present invention may provide a feedback response to the wearer upon a urination event by the wearer. The type of feedback provided may vary, but may include by way of example a wetness sensation response or a temperature response. A temperature response could include one or both of an actual temperature change produced in the article which is transmitted to the wearer's skin or a sensation of warmness or coolness produced without an actual temperature change (or at least not an actual temperature change as great as the perception of temperature change). Temperature change responses can include increases (i.e. warmness) or decreases (i.e. coolness) from the initial or "baseline" temperature prior to the onset of the response. For purposes of clarity, a response producing an actual increase or decrease in temperature in at least a portion of the article will be referred to herein as a "temperature change" or "cooling" or "warming." A response which produces only a sensation of warmness or coolness without an actual corresponding temperature change will be referred to herein as a "warmness sensation" or "coolness sensation."

The feedback response could include multiple sensations such as a combination of wetness and cooling. Other tactile responses such as an effervescent "bubbling" response or an audible or visual response could also be provided. Again, such tactile, audible, or visual responses may be combined with each other as desired. For purposes of clarity "tactile" responses are taken to be those corresponding to the sense of touch or feel. These include temperature change, warmness and coolness sensation, and other physical interaction with the skin responses such as bubbles, physical protrusion of the article, tightness, or the like. "Tactile" responses are distinguished from those which rely on other senses such as hearing, vision, or smell.

Tactile based sensory responses may be preferred to include in the article because a wearer may more readily associate such tactile feedback mechanisms with the triggering urination event. In particular, it may be desired to provide a temperature change response such as a cooling or a warming (or sensations of either or both) as the sensory feedback mechanism. It may be desirable to combine such wetness or temperature (or other) sensory feedback mechanisms with visual or audible response mechanisms to allow participation in the toilet training process by a caregiver or for additional re-enforcement to the wearer. Any of the mechanisms (described in greater detail below) for providing a feedback response to a wearer may be incorporated into any of the embodiments described below for structurally delivering the feedback. As noted previously, it is desirable that the urination triggered feedback responses provided by immediate, temporary, harmless, and unmistakable. Accomplishing these objectives requires control of both the manner in which the signal itself is generated, as well as the manner in which the signal is transmitted to the wearer. The experience of the wearer of the feedback signal will be based upon a combination of the feedback characteristics (such as signal intensity) and transmission characteristics.

For example, if the feedback signal provided is cooling, the experience of the wearer may be determined by a combination of the signal intensity (such as the amount of temperature change a cooling member provides) and the transmission of such coolness to the skin (such as through the pressure and body contact a sensory element member incorporated into the article achieves due to its structure). Articles of the present invention balance both the signal itself and its transmission to the wearer to achieve desirable balance in signal onset, duration, noticeability, and harmlessness.

Figure 3A:
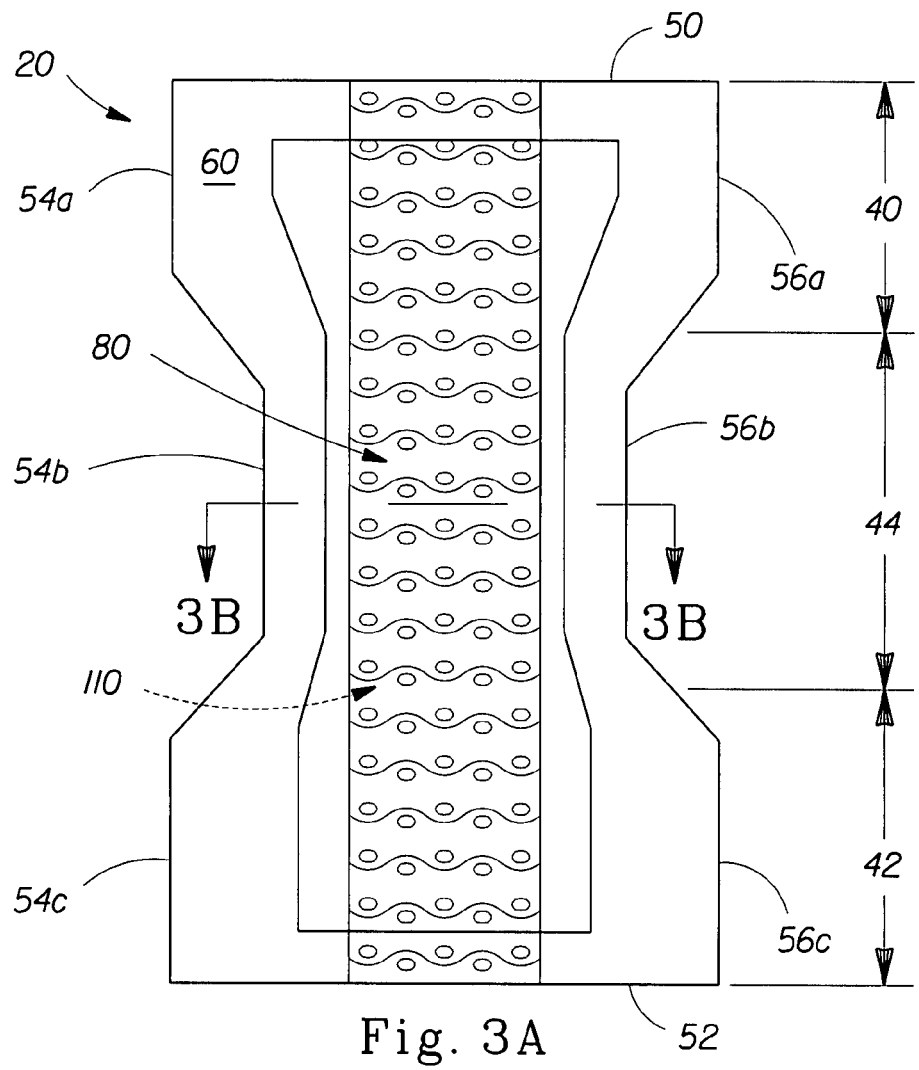
FIG. 3a is a plan view of an absorbent article having a sensory element member according to an embodiment of the present disclosure.
Figure 3B:
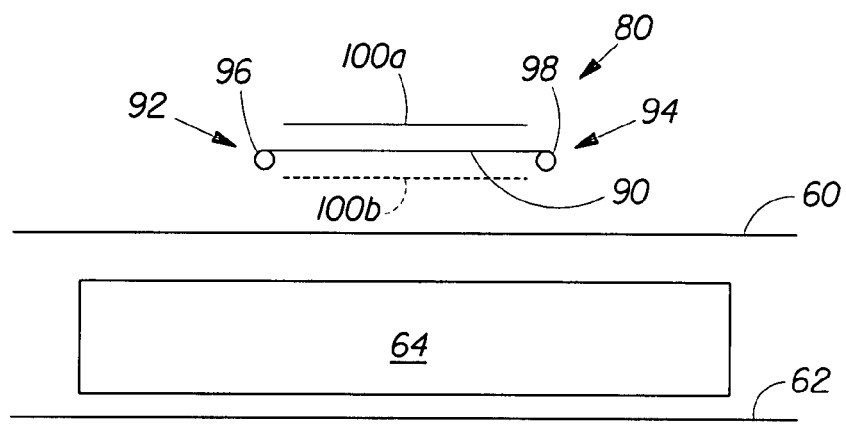
FIG. 3b is a cross-sectional view of the article shown in FIG. 3a illustrating the layers of the sensory element member.
Figure 4A:
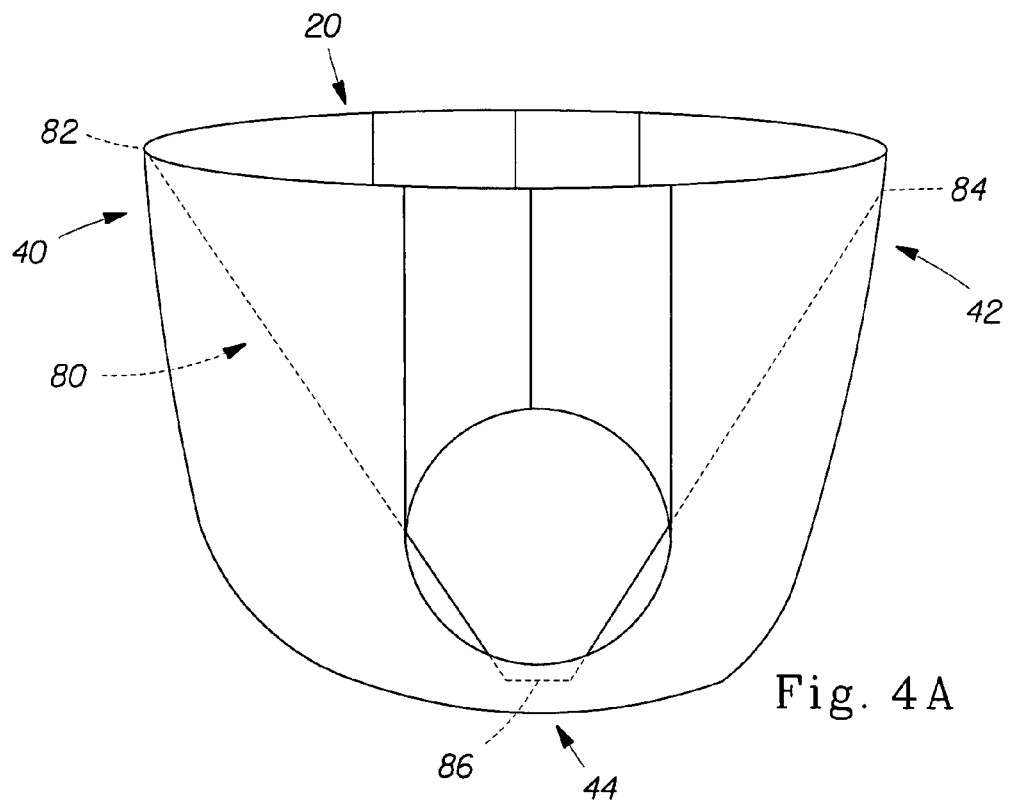
FIG. 4a is an isometric view of the article shown in FIG. 3a illustrating a first exemplary attachment of the sensory element member.
Figure 4B:
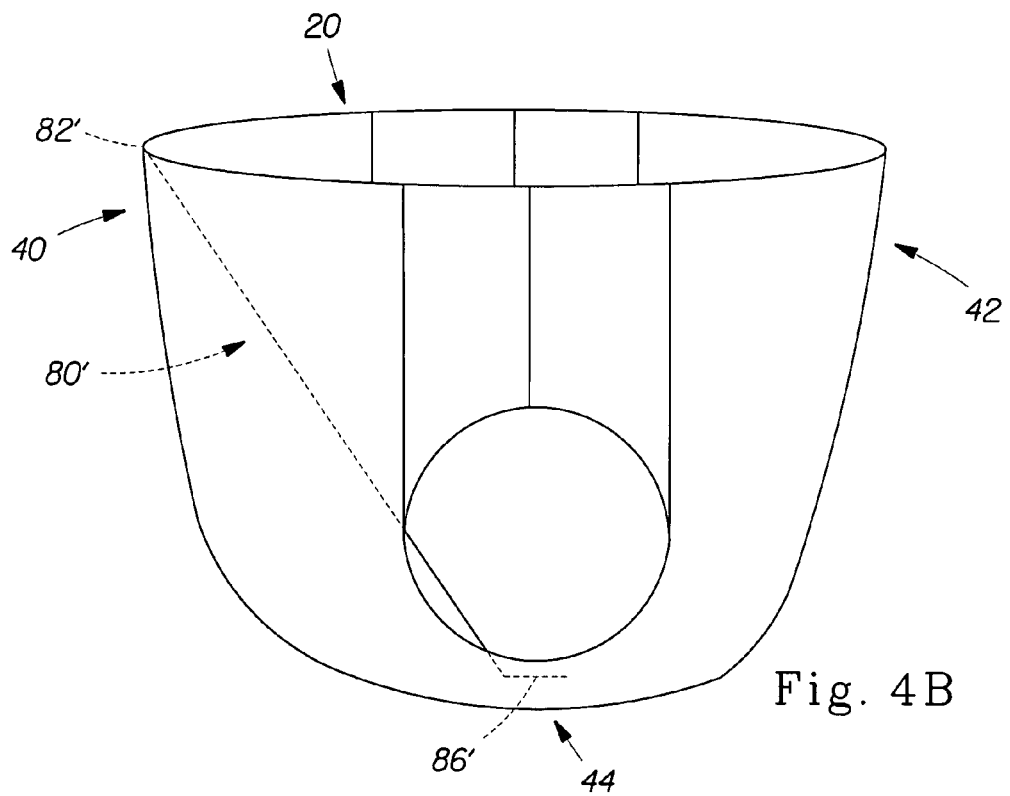
FIG. 4b is an isometric view of the article shown in FIG. 3a illustrating a second exemplary attachment of the sensory element member.

Turning then to the first embodiment of the exemplary sensory element member 80, shown in FIGS. 3a, 3b, and 4a, the sensory element member 80 illustrated is a structure that is formed separately from, but discretely attached to, the topsheet 60. In particular, and as seen best in FIG. 4a, the sensory element member 80 has a first laterally extending joining region or end 82 attached to the first waist region 40, and a second longitudinally opposing and laterally extending joining region or end 84 attached to the second waist region 42. In addition, the sensory element 80 may have a center joining region 86 that may be attached to the crotch region 44. It is believed that the attachment of the sensory element member 80 to the crotch region 44 may assist in stabilizing the member 80, in facilitating fitting of the article 20 to the wearer, in preventing interference with bowel movements and in ensuring good contact of the member 80 with the wearer's skin.

In one embodiment, the sensory element member may provide a urination triggered feedback response based upon a sensation of wetness to the wearer. An example of such a wetness based feedback response is shown in FIG. 3b. As seen in FIG. 3b, the sensory element member 80 may comprise a hydrophilic layer 90, alone or in combination, as explained in greater detail below. Exemplary materials suitable for use in the layer 90 include nonwovens, foams, woven materials, etc. In particular, the layer 90 may comprise, by way of illustration and not limitation, rayon, Lyocell and other cellulose-based materials, cotton, polyester, polypropylene and polypropylene blends (e.g., with other listed materials, such as a Lyocell/polypropylene blend), and hydrophilic forms of nonwovens such as SM (spunbond meltblown), SMS (spunbond meltblown spunbond), and SMMS (spunbond meltblown meltblown spunbond). Exemplary basis weight ranges for these materials are 10-35 gsm and exemplary bulk density ranges are 0.06-0.15 g/cm$^3$. Such materials include Nonwoven Core Cover (10 gsm SSMMS PP) manufactured by Avgol and a Lyocell/PP blend manufactured by Albis with 5-25% Lyocell/75-95% PP (ex. 25 gsm with two layers: 15 gsm philic carded layer with 12 gsm PP and 3 gsm Lyocell; 10 gsm phobic spunbond PP layer below the 15 gsm carded layer).

The layer 90 may have first and second sides 92, 94 that may be parallel to the longitudinal axis 30 of the article 20. Preferably, but not necessarily, a first elastic member 96 may be attached to the layer 90 at the first side 92, while a second 98 elastic member may be attached to the layer 90 at the second side 94. The elastic members 96, 98 may extend along the entire length of the layer 90, or only a portion thereof. A fully or partially elasticized layer 90 may to tend to draw the sensory element member 80 toward or against the skin of the wearer. Alternatively, the layer 90 may be formed to have a lesser length than another layer disposed relatively exteriorly, etc.

In one variation of this embodiment, the sensory element member 80 consists essentially of the hydrophilic layer 90. That is, it may be sufficient for the purpose of alerting the wearer to an insult of urine that a sufficient surface moisture quantity of urine be maintained for a period of time in the layer 90, thereby providing a wetness sensation to the wearer. The Wetness Density (as measured by the Wetness Density Test, below) may range from about 0.4 to about 1.5 grams at 60 seconds.

However, according to other variations of this embodiment, an active component, such as coating or agent, may be applied at 100a, 100b to the layer 90, which may be referred to as a support layer, as illustrated in solid and dashed line. Thus, according to a second variation, the sensory element member 80 may also comprise an active component in the form of a hydrophilic coating, which may be applied at 100a as shown in solid line in FIG. 3b. The hydrophilic coating may be disposed in a face-to-face arrangement with the support layer 90. Moreover, as illustrated, the hydrophilic coating may be disposed on the surface of the layer 90 closer to the wearer's skin (i.e., body-facing surface).

It will be also recognized that the hydrophilic coating may include a diverse range of materials, including lotions, creams and the like. Exemplary hydrophilic coatings include surfactants, such as the NUWET silicone surfactant available from GE Silicones of Wilton, Conn.

Further, according to a third variation, the sensory element member 80 may also comprise an active component in the form of a temperature response element (composition or structure), which may be applied at 100a. The temperature response element may be disposed in face-to-face arrangement with the support layer 90. Moreover, as illustrated, the temperature response element may be disposed on the surface of the layer 90 closer to the wearer's skin (i.e., body-facing surface). Further, the temperature response element may be disposed on the support layer 90 in place of the hydrophilic coating, in conjunction with the hydrophilic coating, or combined (e.g., mixed) with the hydrophilic coating. Further, the temperature response element may be impregnated directly into one or more layers comprising the sensory element member 80 structure such as support layer 90.

It will be recognized that the temperature response element may include those materials that produce a temperature change (i.e., involve an endothermic or an exothermic reaction), as well as those that produce the sensation that a temperature change has occurred without actually producing a temperature change. For example, the temperature response element may be a cooling agent. Further, the cooling agent may be the AQUACOOL dye manufactured by United Polymer Technology of Akron, Ohio. The AQUACOOL dye is a water-soluble dye that changes temperatures when brought into contact with water. An example of a cooling sensation material may be menthol or a menthol derivative, which chemicals are believed to provide the sensation of a temperature change, while not actually producing a temperature change. The COOLACT P and COOLACT 10 products manufactured by LIPO Chemicals of Paterson, N.J. are examples of menthol derivative products which may be suitable. Other examples of suitable temperature change elements and temperature sensation elements may be found in U.S. Pat. No. 6,642,427.

Exemplary suitable sensates that provide a cooling sensation are described in U.S. patent application Ser. No. 10/687,897 filed Oct. 17, 2003 and published Apr. 29, 2004 under Publication No. US20040081680A1; US patent applications 2004/0082654 A1; US 2004/0067970 A1; and US 2005/0049553 A1 and U.S. Pat. Nos. 4,296,255; 4,296,093; 4,226,988; 4,193,936; 4,178,459; 4,153,679; 4,150,052; 4,070,496; 4,070,449; 4,034,109; 4,033,994; 4,032,661; 4,020,153; 4,459,425; 6,267,974; 6,592,884; 6,328,982; 6,359,168; 6,214,788; 5,608,119; and 6,884,906.

Exemplary preferred sensates that provide a cooling sensation described in US 2004/0082654 A1 can be provided alone or in combination, and include ketals such as Frescolat® MGA (available from Symrise), cyclic carboxamides such as WS-3 (available as ISE 3000 from Qaroma, Inc.), aliphatic carboxamides such as WS-23 (available as ISE 1000 from Qarôma, Inc.), cyclohexanol derivatives such as Coolact P® (available from Takasago), and cyclohexyl derivatives such as TK10 (Takasago) and menthyl lactate, also known as Frescolat® ML (Symrise).

Still further suitable sensates that provide a cooling sensation that can be provided alone or in combination include 1-(2-hydroxyphenyl-)-4-(2-nitrophenyl-)-1,2,3,6-tetrahydropyrimidine-2-one, also known as Icilin available from Biomol International, and derivatives thereof; ethyl 3-(p-menthane-3-carboxamido) acetate, also known as WS-5 (available from Millenium Specialty Chemicals as Win-Sense™ Extra); N-(4-methoxyphenyl)-p-menthane-3-carboxamide, also known as WS-12; N-t-butyl-p-menthane-3-carboxamide, also known as WS-14; 1-glyceryl-p-menthane-3-carboxylate, also known as WS-30; ethylene glycol p-menthane-3-carboxylate, also known as WS-4; 3-(1-menthoxy)-2-methylpropane-1,2-diol; geraniol; eucalyptol; linaol; hydroxycitronellal; paramenthane-3,8-diol, also known as PMD-38 (Takasago International); menthyl pyrrolidone carboxlate, also known as Questice® (available from Quest International); 2-isopropyl-5-methylcyclohexyl-4-(dimethylamino)-4-oxobutanoate; (−)-Cubebol; N-(4-cyanomenthylphenyl)-p-menthanecarboxamide; (1R,3R,4S)-3-menthyl-3,6-dioxahieptanoate; (1R,2S,5R)-3-menthyl-methoxyacetate; (1R,2S,5R)-3-menthyl-3,6,9-trioxadecanoate; (1R,2S,5R)-3-menthyl-(2-hydroxyethoxy) acetate; (1R,2S,5R)-menthyl-11-hydroxy-3,6,9-trioxaundacanoate; (−)-Isopulegol; cis and trans p-menthane-3,8-diol, also known as Coolact 38D® (Takasago International); and Cooling Agent 10 from Taksago International menthol and derivatives.

The cooling sensate(s) are desirably delivered to the skin in a form capable of stimulating the cool-sensing nerves immediately (i.e., within 30 seconds, alternatively 15 seconds) subsequent to contact with urine. In one embodiment, the cooling sensate(s) are in solid form and are disposed proximal to, or on, the wearer-facing surface of the article 20. The sensate(s) can dissolve in the urine and thus contact the skin in an aqueous-based phase where they function to stimulate the cool-sensing nerves.

Moreover, according to a fourth variation, the sensation element member 80 may comprise an active component in the form of a hydrophobic coating, which may be applied at 100b as shown in dashed line in FIG. 3b. According to this variation, the hydrophilic coating and/or temperature response element may or may not be included (the temperature response element being combinable with either the hydrophilic or hydrophobic agent, if present). Like the hydrophilic coating, the hydrophobic coating may be disposed in a face-to-face arrangement with the support layer 90. Moreover, as illustrated, the hydrophobic coating may be disposed on the surface of the layer 90 between the layer 90 and the topsheet 60, or the surface further from the wearer's skin (i.e., the opposite surface).

It will be also recognized that the coating 100b may include a diverse range of materials, including lotions, creams etc. Exemplary coatings may comprise hydrophobic coatings (HFC) and liquid-impermeable surface coatings (LISC). In particular, the coating may be made in accordance with the disclosure of U.S. Published Application No. 2005/0177123. Alternatively, the coatings may be acrylic polymer (e.g., acrylamide, ethyl alcohol, n-butyl alcohol, methyl-methacrylate, acrylamide, acrylonitrile, or combinations thereof) emulsions manufactured and sold, for example, under the ROHATOL tradename by Lanxess Corp. of Pittsburgh, Pa., the RH-MW1845K tradename by Rohm & Haas of Philadelphia, Pa., or the FA1, FA2, or FA3 tradenames by PolymerLatex International GmbH of Marl, Germany.

In fact, the hydrophilic and hydrophobic coatings and temperature response elements described above may be used with other sensory element members, as will be discussed below. Moreover, the coatings and agents may be useful in conjunction with the structures described in U.S. Pat. No. 6,627,786, among others. As an alternative to coatings, response agents may be impregnated into any desired structure of the article to provide an integral layer having the desired response functionality.

The spacing of the first and second sides 92, 94 of the layer 90 and the width of the coating, if present, may be determined to allow enough liquid to bypass the sensory element member 80 to the core 64 so as to prevent flooding. Flooding may result in leakage of the article 20 during urination, which is undesirable in the article 20 when it is a diaper or training pant, for example. Consequently, it will be recognized that the dimensions of the layer 90 and coating may be determined to prevent flooding while at the same time wicking sufficient liquid to create a sensation of wetness for the user.

During insults of urine, the layer 90 allows urine to penetrate in the z-direction and also provides a medium for the flow of urine in the x-y plane via wicking. The layer 90 and/or the coating may enhance the movement of the passage of the urine in the x-y plane, thereby expanding the wetted area of the sensory element member, which preferably is held in contact with the wearer's skin. The wicking in the x-y plane causes the urine to spread out and effectively wet a large area before being absorbed into the absorbent assembly, thereby maximizing the wetness signal experienced by the wearer.

It may be desired that the sensory element member 80 be provided with additional ingredients such as a pH buffer, enzyme inhibitors, skin care compositions including Zinc Oxide or any of the exemplary skin benefit ingredients described in U.S. Pat. Nos. 6,118,041 and 6,107,535. Such ingredients can be present to offset any impact of urine being in contact with the skin.

It is desirable that the sensory element and sensory element member provide a feedback response within a short time after the onset of urination. For example, the feedback response may be provided within about 60 seconds of the urination event, or may be provided within about 30 seconds or the urination event, or may be provided within about 15 seconds of the urination event. The time response to feedback onset may vary depending on the type of feedback provided. For example, if the feedback response is a wetness sensation, it may be desired that the article: provide the feedback response within about 30 seconds of the urination event, within about 15 seconds of the urination event, or within about 5 seconds of the urination event. The time response to feedback onset may vary depending on the type of feedback provided. For example, if the feedback response is a wetness sensation, it may be desired that the article provide the feedback response within about 30 seconds of the urination event, or within about 15 seconds of the urination event. If the feedback response is a temperature change or temperature change sensation, it may be desirable to provide the feedback response within about 300 seconds of the urination event, or within about 15 seconds of the urination event, or within about 10 seconds of the urination event. Additionally, if the feedback response is a temperature change, it may be desirable to provide a minimum rate of temperature change to produce the desired noticeability and timeliness of response. The minimum temperature change rate desired at some point in the first 2 minutes following a urination event might be at least about 0.5° C./second, or at least about 1° C./second, or at least about 2° C./second, or at least about 3° C./second, or at least about 5° C./second. The specified rate of temperature change typically is limited to a specific duration in order to prevent the temperature from decreasing into the range of temperatures perceived by the body as noxious cold. The greater the rate of temperature change, the shorter the required duration of the temperature change rate. Typically, the duration of the specified rate of temperature change is in the range of between about 1 second and about 30 seconds, although longer durations are possible depending on the temperature change rate. Preferably, the duration of the specified temperature change rate is in the range of about 2 seconds to about 10 seconds. The temperature may change at some other rate prior to and after the time span defined by the duration specified above. Additionally, in order to provide the wearer a signal correlated as closely as possible to the actual urination event, the specified temperature change rate preferably occurs within the first two minutes, more preferably within the first minute, still more preferably within the first 20 seconds, and most preferably within the first 5 seconds following contact with urine. By the term "occurs" is meant that at least the specified temperature change rate begins within the defined period following urination, although the entire duration of the temperature change rate may fall within the specified timeframe.

For purposes of determining the onset of a feedback response, one or more of the appropriate measurement techniques described below may be used. For example, if the feedback response provided by a particular sensory element in a particular article is a temperature change, the Temperature Change Response Measurement using a thermocouple described below may be used. If the feedback response provided is a wetness sensation, for example, the Wetness Density Test using filter paper described below may be used. These techniques provide one of skill in the art with the ability to determine when a feedback response is deemed to be "provided" (i.e. when it starts) and how long it is deemed to persist for purposes of the present application, including the claims.

If the feedback response is a temperature change, such as a temperature decrease, the temperature change should be of a sufficient magnitude to be noticed by the wearer. A temperature change of at least 5° C. (as measured from body temperate or about 37° C.) might be desired to be noticeable. Cool receptors in the skin are most sensitive at about 25° C. (representing a temperature change of about 12° C. from body temperature). Cool signal activity is still high at 20° C., and the body typically senses "cool" down to about 15° C. Temperatures lower than 10-15° C. are perceived as "cold." It, therefore, may be desirable to provide a temperature change signal greater than about 5° C., preferably about 10-15° C., or a change of up to about 25° C. (as measured in terms of degrees change from body temperature). It may also be desired in some embodiments to have a cold signal (a large temperature change) for children who do not easily perceive more mild "cool" signals. Such a "heavy duty" or less easy to ignore cold signal could be provided by a cooling member which cools the skin to a temperature of less than about 15° C. Skin temperatures of less than 10° C., however, should be avoided since such temperatures are "noxious cold" and start to result in "burning pain." Such signals would not accomplish one of the design objectives of "harmless" described above.

The coolness (or temperature change or temperature change sensation generally) is usually felt as long as the temperature is near the minimum temperature (in the case of coolness) resulting from the cooling agent. Once the temperature begins to increase again (or even when the rate of cooling has declined sufficiently) the cooling becomes imperceptible to the wearer. This is true even if the resulting temperature is lower than the starting temperature. As an example if the skin (or absorbent article surface) is near about 37° C. and is insulted with urine of approximately 37° C., the sensory element member may trigger a temperature change response by cooling the skin to a minimum temperature of about 25° C. within about 30 seconds. As the temperature change effect begins to dissipate, and the temperature rises, the wearer may not perceive coolness once the temperature exceeds about 28° C. It will be appreciated that in this example 28° C. represents a temperature of the minimum temperature (25° C.) plus 25% of the maximum delta T (maximum temperature change initial 37° C. or 12° C. in this example). Therefore, the "duration" of the coolness based feedback may be defined in this example as the time between the urination event and the time when the surface temperature returns to a point at which the temperature change which is no longer greater than 75% of the maximum change. The duration of this time may be about 120 seconds, or less than about 150 seconds, or less than about 300 seconds. Durations under this description of about 30 seconds or about 60 seconds may be acceptable for stronger signals. The duration desired may be inversely related to the signal intensity.

In order to readily compare one article to another when such articles incorporate temperature change based feedback mechanisms, the surface temperature of the article using a thermocouple system (as described in the Temperature Change Response Measurement, below) may be recorded 30 seconds after insulting the article with 75 mL of 0.9% saline at 37° C. A typical desired temperature change at this time may range from about 5° C. to about 20° C.

If the feedback response is a wetness sensation, the amount of moisture contacting the skin should be of a sufficient quantity to be noticed by the wearer. For example, a surface Moisture Density (as measured by the Moisture Density Test) of greater than about 2 mg/cm$^2$ at 60 seconds or greater than about 4 mg/cm$^2$ at 60 seconds or greater than about 5 gm/cm$^2$ at 60 seconds may be desired. The wetness desirably does not persist for an undue period of time. For example, it may be desired that the surface Moisture Density at 10 minutes is less than about 80% or less than about 75% or less than about 70% of the surface Moisture Density measured at 60 seconds.

It is also desirable when designing the sensory element member to take into account the transmission of the feedback signal to the wearer. The signal generated by the sensory element should be incorporated directly or indirectly to a sensory element member which contacts the wearer's skin to elicit a sensation. Ideally, the article and sensory element member are designed to enable at least intermittent, and preferably virtually continuous, contact between the wearer facing surface of the sensory element member and the wearer's skin in all body positions and during all activities in which the wearer may engage. Preferably, the area of contact on the wearer's body is an area having a relatively higher concentration of nerve endings. In the region of the body commonly covered by disposable absorbent articles such as pant-like diapers or training pants, the genital, perineal, perianal, inner thigh, and lower abdomen have a relatively higher nerve concentration are the preferred contact areas.

One preferred method of promoting contact between the sensory element member and the wearer is to provide a raised sensory element member as described herein. In these embodiments, the skin contact is effected by providing a sensory element member at least locally detached from underlaying layers in at least the desired region of contact and elastically foreshortening the sensory member, or a structure to which the sensory element member is affixed, causing the sensory element member to be lifted in the z-direction toward the body. Additionally, in certain embodiments, the elastic lifting members cause the sensory element member to contact the body with sufficient force and resiliency to allow the sensory element member to continue to contact the body during wearer motion, or to quickly re-establish contact in the event that contact is temporarily broken Other methods of promoting skin contact may also be employed in place of, or in addition to the method described hereinabove. For example, at least a portion of the skin contacting surface of the article may comprise a contact promoting substance that adheres gently to the wearer's skin and resists casual disengagement. Exemplary contact promoting substances may include skin care compositions such as lotion as described in U.S. Pat. Nos. 5,607,760; 5,609,587; 5,635,191; 5,643,588; 5,968,025; 6,118,041; 6,120,488; 6,120,783; 6,153,209; 6,156,024; and 6,166,285, sticky lotions as described in International Patent Application WO 2004/087092, and adhesives such as body adhesives. In certain embodiments a water-activatable adhesive may be desirable as it would only promote contact once the wearer urinates. Water activatable adhesives for use in disposable absorbent articles are disclosed in U.S. Pat. No. 6,623,465. The skin contact promoting substance may be disposed on at least a portion of the sensation member 80 or in a region of the topsheet 60 or other supporting structure in proximity to the sensory element member 80.

Skin contact may also be promoted via resilient 3-dimensional structures comprising foams or core materials. These structures serve to hold the sensory element member in contact with the wearer even during wearer motion due to their 3-dimensional resilient nature. In some embodiments, these structures may be relatively thin and unobtrusive when in a dry state and may be triggered to grow in the z-direction by contact with urine. For example, the structure may comprise a compressed foam encapsulated in a water or pH sensitive material wherein the foam is allowed to expand upon contact with urine or the structure may comprise a composition capable of evolving gas held within a semi-permeable membrane such that it inflates upon contact with urine. Further examples of structures that increase in thickness upon contact with urine include those described in U.S. Pat. Nos. 3,881,491; 3,921,232; 5,330,459; 6,186,991; 5,797,892; 5,428,076; and 5,124,188.

The physical structure of the sensory element member, its body contact area, and force of contact may vary depending upon the type of signal, intensity of signal, and coupling of the sensory element to the sensory element member. For example, if the feedback signal is a temperature change element, the amount of temperature change element needed depends upon the degree of temperature change provided its location in the article, and how much surface area having such temperature change element is provided in a body contacting structural member in any given body position. It has been found during development of the present invention that using the temperature change mechanisms described above, for example, that the desired cool signal is provided when the body contacting portion of the sensory element member has an area of greater than about 25 cm², or greater than about 50 cm², or greater than about 100 cm². In general, the greater the surface area of the sensory element member body contacting portion, the less intense the signal itself need be to produce the desired result. One of skill in the art will also recognize that the degree of coupling of the sensory element to the sensory member will also affect the desired body contact. For example, a temperature change sensory element directly impregnated onto the top surface of the sensory element member may more readily transmit the signal to the skin than a temperature change sensory element disposed in an underlying layer which cools the sensory element member which in turn cools the skin. In the later case, the indirect transmission of the signal may lead to greater desired body contact area and/or force of contact by the sensory element member.

The disposable absorbent article 20 may have visible highlighting, indicated at 110 in FIG. 3a and illustrated as an exemplary pattern of wavy lines and circles, in the interior of the article associated with the sensory element member or members 80 to indicate the presence of the sensory element member or members 80 and thereby facilitate an opportunity for the urinary toilet training of the wearer of the article. Such visible highlighting is described in U.S. Published Application No. 2005/0096612. Although a sensory element lacking this visible highlighting is fully functional in terms of providing a noticeable wetness and/or temperature signal to the wearer, the caregiver might overlook or forget the possibility of capitalizing on each opportunity for urinary toilet training if the body-facing portion of the absorbent article presents a generally uniform appearance, such as in absorbent articles that present a generally uniform white appearance on their body-facing surfaces.

Furthermore, once the caregiver decides to mention urinary toilet training to the wearer, the visible highlighting can serve to draw the wearer's interest or can be pointed out by the caregiver and incorporated into an explanation of the upcoming opportunity. Thus, the visible highlighting can provide a topic for conversation between the caregiver and the wearer on the subject of urinary toilet training and can likewise provide a nameable object for reference by the wearer, greatly simplifying the mental task required of the wearer who desires to communicate his or her need to go to the toilet or to communicate his or her improving recognition of the wetness signal provided by the sensory element member.

Even a simple solid coloring form of visible highlighting can serve to facilitate an opportunity for urinary toilet training, especially when used with wearers possessing some recognition of colors or colored forms. In addition, visible highlighting in the form of a color or colors may facilitate the teaching of recognition of colors and differences between colors, and the associated learning may enhance the urinary toilet training process in turn.

In addition, the visible highlighting can serve to enhance the self-esteem of the wearer through a reminder that he or she is mature enough to be engaged in urinary toilet training. This effect can be compounded when the wearer succeeds in recognizing the need to go to the toilet and then sees the dry condition of the visibly highlighted sensory element member inside the article after pulling it down.

The visible highlighting may be provided by means of printing onto a surface of the sensory element member or one of its layers. For example, solid coloring or a graphic may be printed onto a surface of the coating underlying the water-permeable layer. As another example, an adhesive or a gel may be printed onto a surface of either of the two layers. Such an adhesive or gel may be colored differently from the surrounding area. Alternatively, the adhesive or gel may be uncolored or may have the same color as the surrounding area, but may still provide visible highlighting by forming a distinctive raised area or pattern and/or by surrounding a distinctive recessed area or pattern.

In addition to visible highlighting on the sensory element member itself, visible highlighting or other graphical elements can be provided elsewhere on the article. This can be in addition to or instead of on the sensory element member.

In some embodiments, the visible highlighting may become more or less visible when the sensation member is wetted. In addition, the visible highlighting may change color when the sensation member is wetted. Any of these effects may be created by the use of inks or dyes or other agents that undergo chemical reactions or are dispersed or concentrated when wetted by urine. In general, any of the wetness indicating compositions commonly used in externally visible wetness indicators, such as so-called "appearing" or "disappearing" wetness indicators that may become more or less visible when wetted and in wetness indicators that may change color when wetted, may be used for these versions of visible highlighting.

Wetness indicating compositions used for the visible highlighting of the sensory element member may be visible from the body-facing surface of the absorbent article or may be included in the article so as to be visible from the outside, or from both. If the wetness sensation member is disposed on the interior surface of the article, a caregiver might apply different techniques to the task of urinary toilet training as compared to using an absorbent article having only a wetness indicator visible from the outside of the article. For example, while the change in an exterior wetness indicator is visible for all to see, any change in the visible highlighting of an interior sensory element member remains "private" until either the caregiver or the wearer peers into the absorbent article or it is removed. Either or both approaches can be used or interchanged as desired to re-enforce the other training features described herein.

The article 20 may comprise an internal graphic 110, a first external graphic, and a second external graphic. The internal graphic may be permanent, while the external graphics may be: "appearing" or "disappearing." The first external graphics may include a character image resembling a boy and a text graphic including words forming a message, such as "Remember to go to the potty!" While the graphics may include text, the primary form of communication may be symbols, icons, or other markings other than words, so that a pre-literate child may comprehend and follow the instructions or other information indicated by the graphics, although it is not necessary for the images to be understood at this level. The second external graphics may include an image that may be associatively correlated to the permanent graphic, such as a dog or stars.

Variations regarding the internal/external graphics are possible. For example, a permanent external image may be combined with the first and second external graphics, or only one external graphic may be included. Furthermore, character images other than a boy may be provided, such as a girl, an animal (which may be anthropomorphic), a cartoon character, and the like. Still further, additional or alternative text may be provided. Additionally exemplary graphics, graphics characteristics and/or arrangements (e.g., timings, themes, scenes, storylines, etc.), the materials that are suitable for forming the graphics, and the arrangement and/or joining of these materials to the article 20 are described in co-pending and commonly assigned U.S. patent application Ser. No. 11/098,362, filed in the name of Roe et al. on Apr. 4, 2005.

Even in embodiments in which the appearance of the visible highlighting is not affected by its being wetted, the associative correlation of the respective visible forms of an externally visible marking and the visible highlighting may serve to facilitate an opportunity for urinary toilet training. For example, if both the externally visible marking and the visible highlighting have the visible form of similar graphics, the externally visible marking can serve to draw the wearer's interest or can be pointed out by the caregiver and incorporated into an explanation of the ongoing opportunity for urinary toilet training.

Figure 5A:
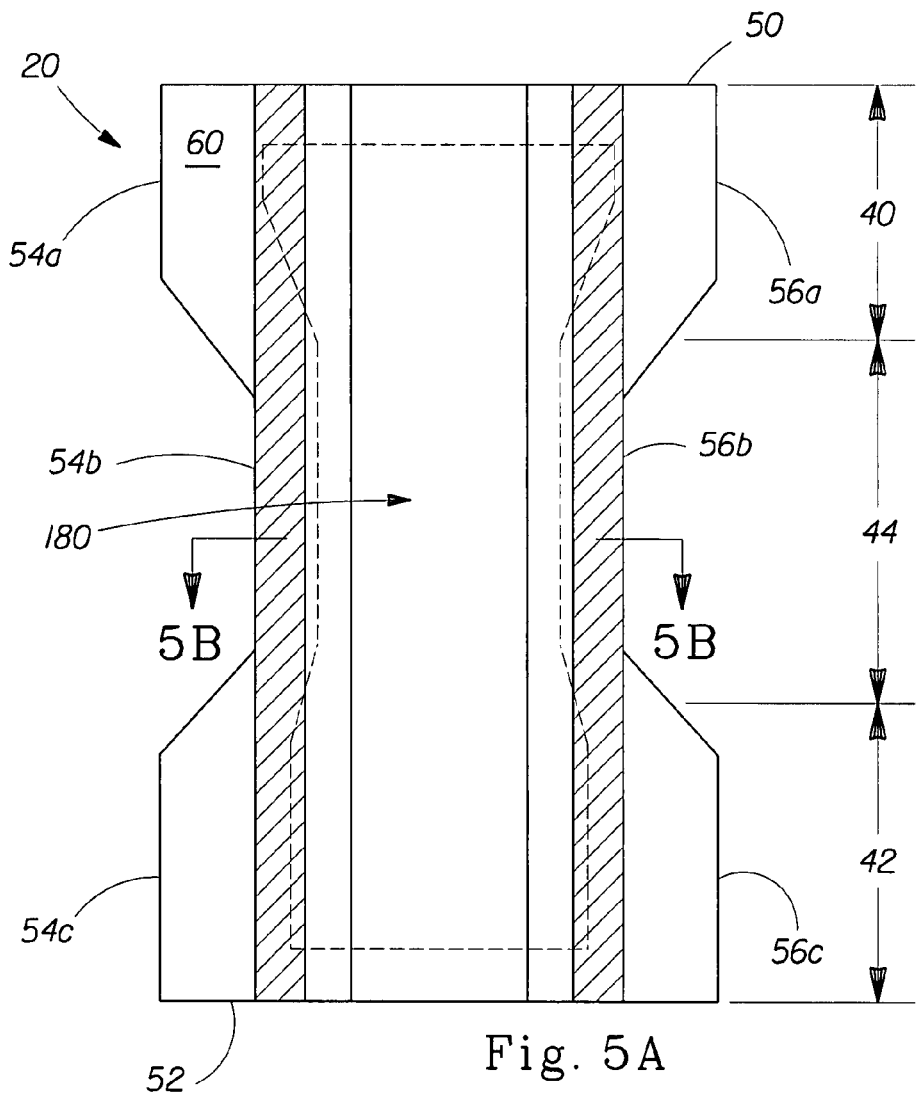
FIG. 5a is a plan view of an absorbent article having a sensory element according to another embodiment of the present disclosure.
Figure 5B:
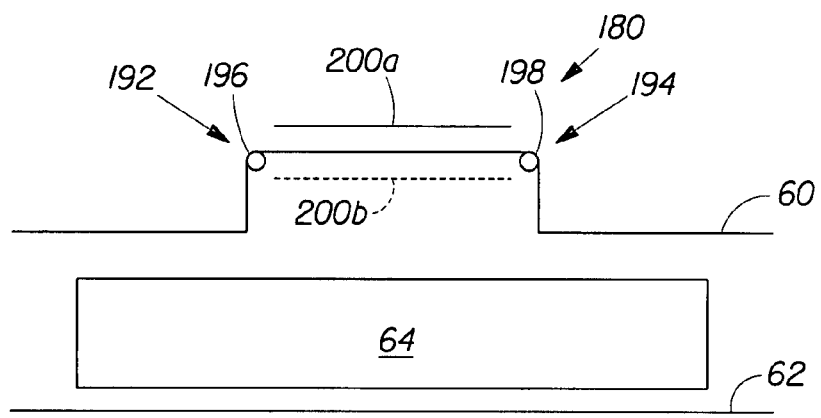
FIG. 5b is a cross-sectional view of the article shown in FIG. 5a illustrating the layers of the sensory element member.

Turning next to FIGS. 5a and 5b, a second embodiment of a sensory element member 180 is illustrated therein. Similar to the sensory element 80, the sensory element member 180 has first and second sides 192, 194 that are arranged parallel to the longitudinal axis 30 of the article 20. Moreover, elastic members 196, 198 may be attached to the sensory element member 180 at the sides 192, 194 so as to elasticize the sensory element member 180, which may assist in bringing the sensory element member 180 into close contact with the skin of the wearer, increasing the efficacy and reliability of the signal transfer to the skin. Further, the sensory element may include an active component, such as (i) a coating, which may be a hydrophilic coating disposed on a body-facing surface or a hydrophobic coating disposed on an opposite surface, (ii) a temperature sensation element, which may be disposed on either surface and in substitution for, in conjunction with, or combined with the coating, and/or (iii) a layer of hydrophilic material, such as was described relative to the layer 90 above and which also may be disposed on a body-facing surface.

The sensory element member 180 differs from the sensory element member 80 in that the structure corresponding to the support layer 90 is formed from a section of the topsheet 60 spaced from the core 64. That is, a section of the topsheet 60 is folded to define support layer structure of the member 180, and, in particular, is folded along the sides 192, 194. The elastic members 196, 198 are then disposed beneath the topsheet 60 in the space between the topsheet 60 and the core 64. In this fashion, the sensory element member 180 may be integrated to a greater degree to the remainder of the article 20 than the member 80, thereby reducing the likelihood that the sensory element member 180 will become detached from the remainder of the article 20.

The sensory element member 180 may include other features in common with the sensory element member 80. For example, the coatings and agents disposed at 200a, 200b may include those exemplary coatings and agents listed above. Moreover, while not illustrated, a visible graphic 110 may be include on a surface of the sensory element member 180, providing one or more of the advantages discussed above.

Figure 6A:
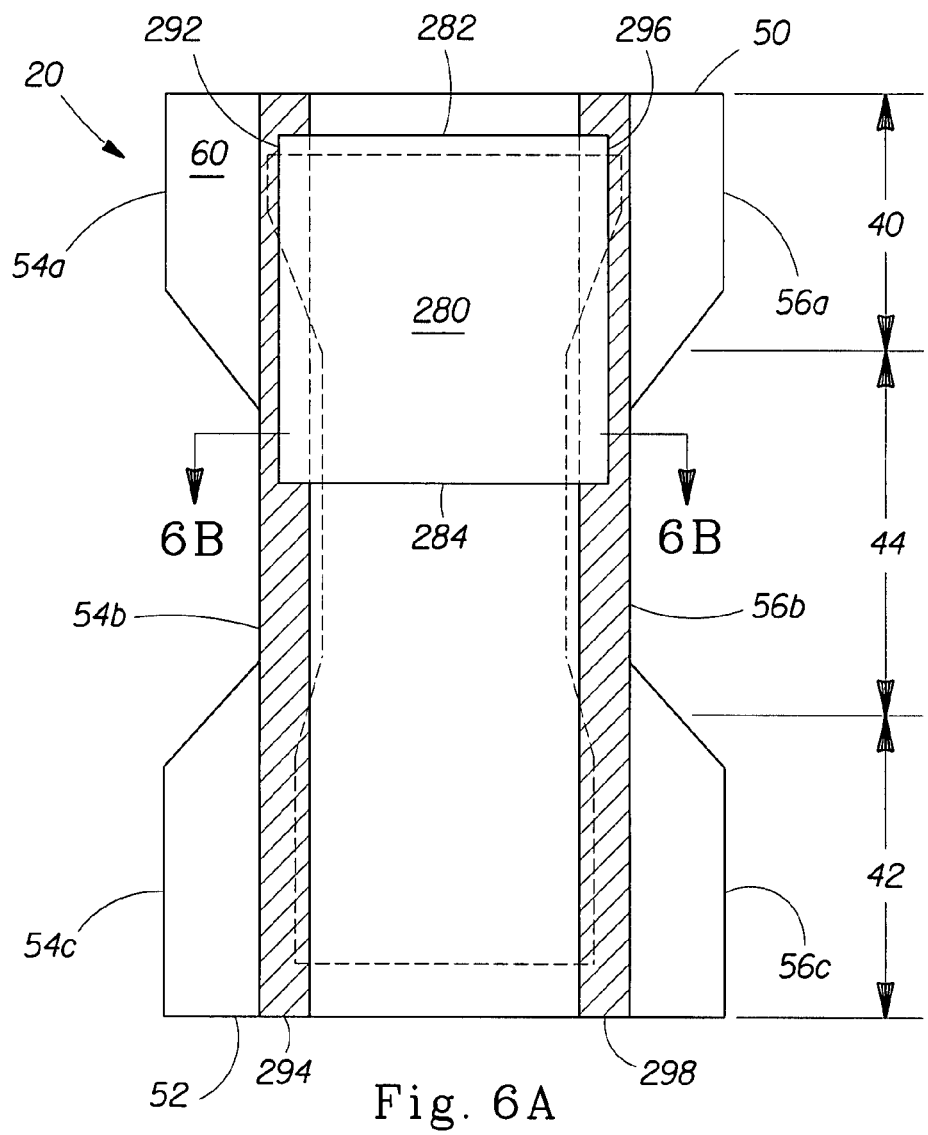
FIG. 6a is a plan view of an absorbent article having a sensory element member according to a further embodiment of the present disclosure.
Figure 6B:
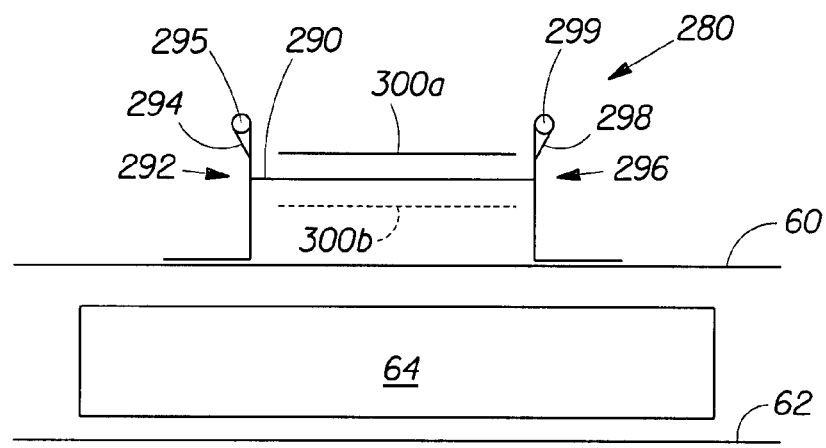
FIG. 6b is a cross-sectional view of the article shown in FIG. 6a illustrating the layers of the sensory element member.

Turning then to FIGS. 6a and 6b, a third embodiment of the sensory element member 280 is illustrated, with the barrier leg cuffs folded back slightly in FIG. 6a to expose the sensory element member 280. The sensory element member 280 has a first laterally extending end 282 and a second longitudinally opposing and laterally extending end 284. As will be recognized, the distance between the ends 282, 284 is shorter than the distance between the ends 50, 52, or even the distance between end 50 and the crotch region 44. According to the embodiment, the position of the ends 282, 284 relative to the ends 50, 52 and the spacing between the ends 282, 284 is such that the likelihood that the sensory element member 280 will be wetted with urine is enhanced.

The sensory element member 280 includes a layer 290. The layer 290 extends between the ends 282, 284. Additionally, a first longitudinal edge 292 of the layer 290 is attached to a first barrier leg cuff 294 attached to the topsheet 60, while a laterally opposed, longitudinal edge 296 is attached to a second, spaced barrier leg cuff 298, also attached to the topsheet 60. Moreover, each barrier leg cuff 294, 298 includes an elastic member 295, 299. In this fashion, it is not necessary to attach separate elastic members to the support layer 290, but the elastic members 295, 299 of the barrier leg cuffs 294, 298 instead may urge the sensory element 280 into contact with the skin of the wearer.

In fact, it is believed that the attachment of the sensory element member 280 to the barrier leg cuffs 294, 298 may permit greater control over the spacing of the sensory element member 280 relative to the topsheet 60 (i.e., distance between member 280 and topsheet 60) than had heretofore been possible. That is, by attaching the sensory element 280 along its sides 292, 296, rather than at its ends 282, 284, the spacing of the member 280 relative to the topsheet 60 may be better controlled than in those embodiments wherein the member is attached at its ends, or potentially even in those embodiments where the member is integrated into the topsheet 60 and elastic members disposed internal to the topsheet 60 are used to define, at least in part, the sensory element. Additionally, by attaching the sensory element member 280 to the leg cuffs 294, 298, the dimension of the sensory element member 280 perpendicular to the longitudinal axis may be greater than, for example, the sensory element members 80, 180 discussed above.

Similar to the embodiment shown in FIGS. 3a and 3b, the sensory element member 280 may consist essentially of the layer 290, or may comprise the layer 290 in combination with a coating or an agent, which coating or agent may be disposed in a face-to-face arrangement with the layer 290, which may be referred to as a support layer. The coating may be a hydrophilic coating disposed at 300a on the body-facing surface of the layer 290, or a hydrophobic coating disposed at 300b on the opposite surface. Additionally, a temperature sensation element may be disposed at 300a on either surface and in substitution for, in conjunction with, or combined with the coating.

The sensory element member 280 may include other features in common with the sensory element members 80, 180. For example, the coatings and agents may include those exemplary coatings and agents listed above. Additionally, while not illustrated, a visible graphic 110 may be include on a surface of the sensory element member 280, providing one or more of the advantages discussed above.

In additional embodiments shown in FIGS. 7a-7c, the sensation member 380 or any layer including the sensation member can be disposed in two parallel Z-folds 387 formed along the longitudinal length of the absorbent article. The Z-folded sensation member 380 or any layer including the sensation member may be attached to the underlying layers along the longitudinal edges of the topsheet 60 allowing the portion between the Z-folds of the topsheet 60 to float freely. Elastic elements 96, 98 may be disposed along the central region of the sensation member 380 in order to deflect the central region outward away from the absorbent core 64. Elastic elements 96, 98 may be disposed between layers of the topsheet 60, between layers of the sensation member 380, between the topsheet 60 and sensation member 380, or any other configuration that connects the elastic elements 96, 98 to the topsheet 60 and/or sensation member 380. The central region 385 may have a first side edge 385a and a second side edge 385b such that at least one of said side edges 385a, 385b has a projected height h measured the z direction between the side edge and the base of the sensation member that connects the sensation member to the absorbent article.

A disposable absorbent article including a sensation member is attached to the inner surface of a curved plate (i.e. the concave surface relative to the hypothetical center of the circle having the same curvature as the plate) having a radius of curvature of about 250 mm. The disposable absorbent article is attached to the plate such that its garment facing surface (i.e. outer cover) is in contact with the plate. In this configuration, the elastic member(s) that are disposed longitudinally on the disposable absorbent article are in an elongated configuration and are applying a force that is pulling any layer attached to the elastic member away from the core. A ruler having one end contacting the base of the sensation member and the other end pointing toward the center of the hypothetical circle formed by the curved plate, may be used to measure the distance between the base of the sensation and the side edge of the sensation member.

The Z-folded sensation member 380 allows the central region 385 to be suspended away from the core 64 and the topsheet 60. The combination of the Z-folded sensation member 380 and the elastic elements 96, 98 maintains the sensation members in proximity to the wearer's skin in the event that the diaper sags or fits loosely around the wearer.

Alternatively, additional elastic elements 96a, 98a may be disposed along the central region of the Z-folded sensation member. Elastic elements 96a, 98a, may be disposed between layers of topsheet 60, between layers of the sensation member 380, between the topsheet 60 and sensation member 380, or any other configuration that connects the elastic elements 96a, 98a to the topsheet 60 and/or sensation member 380. Elastic elements 96a, 98a provide additional support to prevent sagging and promote contact with the wearer's skin.

The absorbent article may also include a first barrier leg cuff 394 and a second barrier leg cuff 398, which may include elastic members 395, 399 respectively. First and second barrier leg cuffs are disposed on the absorbent article such that the Z-folded sensation member 380 is located between the barrier leg cuffs 395, 399. At least one of the first barrier leg cuff 394 and a second barrier leg cuff 398 has a projected height H measured the z direction between an upper edge of the barrier leg cuff and the base of the barrier leg cuff that connects the barrier leg cuff to the absorbent article.

The projected height h and H may be measured according the following method.

A disposable absorbent article including a sensation member is attached to the inner surface of a curved plate (i.e. the concave surface relative to the hypothetical center of the circle having the same curvature as the plate) having a radius of curvature of about 250 mm. The disposable absorbent article is attached to the plate such that its garment facing surface (i.e. outer cover) is in contact with the plate. In this configuration, the elastic member(s) that are disposed longitudinally on the disposable absorbent article are in an elongated configuration and are applying a force that is pulling any layer attached to the elastic member away from the core. A ruler having one end contacting the base of the sensation member and the other end pointing toward the center of the hypothetical circle formed by the curved plate, may be used to measure the distance between the base of the sensation and the side edge of the sensation member. The side edge of the sensation member is gently extended to its maximum height (i.e. without applying a force that would cause the sensation member to be torn or destroyed) and then record the measurement. The projected height measurement can be repeated at various points along the sensation member in order to determine its maximum projected height. The ruler may be moved such that one end is in contact with the base of an outer leg cuff and its other end is pointing towards the center of the hypothetical circle passing through the curved plate. The projected height H may be determined by measuring distance between the base of the outer leg cuff and the upper edge of the outer leg cuff. The upper edge of the outer leg cuff is gently extended to its maximum height (i.e. without applying a force that would cause the outer leg cuff to be torn or destroyed) and then record the measurement. The projected height measurement can be repeated at various points along the outer leg cuff in order to determine its maximum projected height.

In one embodiment, the projected height h of at least one of the first side edge 385a and a second side edge 385b is between 90% and 300%, preferably between 100% and 250%, more preferably between 100% and 200% of the projected height H of at least one of the first barrier leg cuff 394 and a second barrier leg cuff 398.

In one embodiment, the projected height h of at least one of the first side edge 385a and a second side edge 385b is between 15 mm and 50 mm, preferably between 20 mm and 45 mm, more preferably between 25 mm and 40 mm.

In addition to the features described above, the disposable absorbent article 20 may also include a variety of features known in the art, such as slit openings, outer leg cuffs, front and rear ear panels, waist cap features, elastics, and the like to provide desired fit, containment, and aesthetic characteristics. Such additional features are well known in the art and are described in U.S. Pat. Nos. 3,860,003; 5,151,092; and 6,482,191 among others. Additionally, a transfer layer, which may also be referred to as an acquisition or distribution layer, may be disposed between the topsheet 60 and the core 64. Moreover, the elements discussed above may be modified from their illustrated forms.

Various sublayers may be disposed between the topsheet and the outer cover. The sublayer may be any material or structure capable of accepting, storing or immobilizing bodily exudates. Thus, the sublayer may include a single material or a number of materials operatively associated with each other. Further, the sublayer may be integral with another element of the pull-on garment or may be one or more separate elements attached directly or indirectly with one or more elements of the disposable absorbent article. Further, the sublayer may include a structure that is separate from the absorbent core or may include or be part of at least a portion of the absorbent core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

In embodiments of the present disclosure, a disposable wearable absorbent article can include a stretchable outer cover. For example, the outer cover can be a uniaxially stretchable outer cover, configured to stretch in one direction. Also as an example, the outer cover can be a biaxially stretchable outer cover, configured to stretch in two directions. In various embodiments, the outer cover can be configured as described in U.S. non-provisional patent application entitled "Biaxially Stretchable Outer Cover for an Absorbent Article," filed on Nov. 15, 2006 with Express Mail No. EV916939625 and further identified by attorney docket number 10643, which is hereby incorporated by reference.

In embodiments of the present disclosure, a disposable wearable absorbent can include an outer cover configured in various ways, including configurations of part or all of the outer cover as stretchable, non-stretchable, with an elastic nonwoven, with an elastic film and extensible nonwoven, with an extensible film and an elastic nonwoven, prestretched with elastic strands allowed to contract, mechanically activated, with zero strain laminate, and/or combinations of these and any other outer cover configurations. In various embodiments of the present disclosure, a disposable wearable absorbent article can include a printed outer cover with various basis weights, chemistries, and/or mechanical activations, as will be understood by one of ordinary skill in the art.

Embodiments of the present invention may include acquisition layers and dusting layers, each of which are well known in the art. Acquisition layer are further discussed in U.S. Pat. No. 5,460,622. Dusting layers are further discussed in U.S. Pat. No. 4,888,231. Examples of suitable configurations for leg cuffs are described in U.S. Pat. Nos. 3,860,003; 4,909, 803; and 4,695,278.

One preferred embodiment of the present invention includes, but is not limited to, articles described in U.S. Patent Application No. 2004/0162536 and U.S. Patent Application No. 2004/0167486. The aforementioned applications are directed to absorbent articles having an absorbent core which imparts increased wearing comfort to the article and makes it thin and dry. As shown in FIG. 8, the absorbent articles of the present invention may comprise an absorbent core 64 comprising a substrate layer 400, absorbent polymer material 410 and a fibrous layer of adhesive 420. The substrate layer 400 is preferably provided from a non-woven material, preferred non-wovens include those provided from synthetic fibers, such as PE, PET and PP. As the polymers used for non-woven production are inherently hydrophobic, they are preferably coated with hydrophilic coatings.

In accordance with the present invention, the absorbent material is immobilized when wet such that the absorbent core achieves a wet immobilization of more than 50%, preferably of more than 60%, 70%, 80% or 90%.

The substrate layer 400 comprises a first surface and a second surface. At least portions of the first surface of the substrate layer 400 are in direct contact with a layer of absorbent polymer material 410. This layer of absorbent polymer material 410 is preferably a discontinuous layer, and comprises a first surface and a second surface. As used herein, a discontinuous layer is a layer comprising openings. Typically, these openings have a diameter or largest span of less than 10 mm, preferably less than 5 mm, 3 mm, 2 mm and a span of more than 0.5 mm, 1 mm or 1.5 mm. At least portions of the second surface of the absorbent polymer material layer 410 are in contact with at least portions of the first surface of the substrate layer material 400. The first surface of the absorbent polymer material 410 defines a certain height 412 of the layer of absorbent polymer above the first surface of the layer of substrate material 400. When the absorbent polymer material layer 410 is provided as a discontinuous layer, portions of the first surface of the substrate layer 400 are not covered by absorbent polymer material 410. The absorbent core 64 further comprises a thermoplastic composition 420. This thermoplastic composition 420 serves to at least partially immobilize the absorbent polymer material 410.

In one preferred embodiment of the present invention the thermoplastic composition 420 can be disposed essentially uniformly within the polymeric absorbent material 410.

However, in an even more preferred embodiment of the present invention the thermoplastic material 420 is provided as a fibrous layer which is partially in contact with the absorbent polymer material 410 and partially in contact with the substrate layer 400. In this preferred structure the absorbent polymer material layer 410 is provided as a discontinuous layer, a layer of fibrous thermoplastic material 420 is laid down onto the layer of absorbent polymeric material 410, such that the thermoplastic layer 420 is in direct contact with the first surface of the layer of absorbent polymer material 410, but also in direct contact with the first surface of the substrate layer 400, where the substrate layer is not covered by the absorbent polymeric material 410. This imparts an essentially three-dimensional structure to the fibrous layer of thermoplastic material 420 which in itself is essentially a two-dimensional structure of relatively small thickness (in z-direction), as compared to the extension in x- and y-direction. In other words, the fibrous thermoplastic material layer 420 undulates between the first surface of the absorbent polymer material 410 and the first surface of the substrate layer 400.

Thereby, the thermoplastic material 420 provides cavities to hold the absorbent polymer material 410, and thereby immobilizes this material. In a further aspect, the thermoplastic material 420 bonds to the substrate 400 and thus affixes the absorbent polymer material 410 to the substrate 400. Highly preferred thermoplastic materials will also penetrate into both the absorbent polymer material 410 and the substrate layer 400, thus providing for further immobilization and affixation.

Of course, while the thermoplastic materials disclosed herein provide a much improved wet immobilization (i.e., immobilization of absorbent material when the article is wet or at least partially loaded), these thermoplastic materials also provide a very good immobilization of absorbent material when the article is dry.

In accordance with the present invention, the absorbent polymer material 410 may also be mixed:, with absorbent fibrous material, such as airfelt material, which can provide a matrix for further immobilization of the super-absorbent polymer material. However, preferably a relatively low amount of fibrous cellulose material is used, preferably less than 40 weight %, 20 weight %, or 10 weight % of cellulose fibrous material as compared to the weight of absorbent polymer material 410. Substantially airfelt free cores are preferred. As used herein, the term "absorbent fibrous material" is not meant to refer to any thermoplastic material 420 even if such thermoplastic material is fiberized and partially absorbent.

The absorbent core of the present invention may further comprise a cover layer. This cover layer may be provided of the same material as the substrate layer 400, or may be provided from a different material. Preferred materials for the cover layer are the non-woven materials. In this embodiment, portions of the cover layer bond to portions of the substrate layer 400 via the thermoplastic material 420. Thereby, the substrate layer 400 together with the cover layer provides cavities to immobilize the absorbent polymer material 410.

The areas of direct contact between the thermoplastic material 420 and the substrate material 400 are referred to as areas of junction 440. The shape, number, and disposition of the areas of junction 440 will influence the immobilization of the absorbent polymer material 410. The areas of junction can be of squared, rectangular, or circular shape. Preferred areas of junction are of circular shape. Preferably, they have a diameter of more than 0.5 mm, or 1 mm, or 1.5 mm and of less than 10 mm, or 5 mm, or 3 mm, or 2 mm. If the areas of junction 440 are not of circular shape, they preferably are of a size as to fit inside a circle of any of the preferred diameters given above.

The areas of junction 440 can be disposed in a regular or irregular pattern. For example, the areas of junction 440 may be disposed along lines. These lines may be aligned with the longitudinal axis of the absorbent core, or alternatively, they may have a certain angle in respect to the longitudinal edges of the core. It has been found, that a disposition along lines parallel with the longitudinal edges of the absorbent core 64 create channels in the longitudinal direction which lead to a lesser wet immobilization. Preferably, therefore the areas of junction 440 are arranged along lines which form an angle of 20 degree, 30 degree, 40 degree, or 45 degree with the lonigitudinal edges of the absorbent core 64. Another preferred pattern for the areas of junction 440 is a pattern comprising polygons, for example pentagons and hexagons or a combination of pentagons and hexagons. Also preferred are irregular patterns of areas of junction 440, which also have been found to give a good wet immobilization.

Two fundamentally different patterns of areas of junctions 440 can be chosen in accordance with the present invention. In one embodiment, the areas of junctions are discrete. They are positioned within the areas of absorbent material, like islands in a sea. The areas of absorbent materials are then referred to as connected areas. In an alternative embodiment, the areas of junctions can be connected. Then, the absorbent material can be deposited in a discrete pattern, or in other words the absorbent material represents islands in a sea of thermoplastic material 420. Hence, a discontinuous layer of absorbent polymer material 410 may comprise connected areas of absorbent polymer material 410 or may comprise discrete areas of absorbent polymer material 410.

In a further aspect of the present invention, it has been found that absorbent cores providing for a good wet immobilization can be formed by combining two layers. In this embodiment, the absorbent core material comprises two substrate layers 400, two layers of absorbent polymer material 410 and two layers of fibrous thermoplastic materials 420. When two discontinuous layers of an absorbent polymer material 410 are used, they would be typically arranged in such a way that the absorbent polymer material of the one layer faces the areas of junction 440 of the other layer. In an alternative preferred embodiment, however, the areas of junction 440 are offset and do not face each other.

According to the present invention, the thermoplastic layer 420 can comprise any thermoplastic composition, preferred are adhesive thermoplastic compositions, also referred to as hot melt adhesives. A variety of thermoplastic compositions are suitable to immobilize absorbent material. Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behaviour are herein also understood as thermoplastic materials 420.

Embodiments of the present invention may also include pockets for receiving and containing waste, spacers which provide voids for waste, barriers for limiting the movement of waste in the article, compartments or voids which accept and contain waste materials deposited in the pull-on garment, and the like, or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids in an absorbent article are disclosed in U.S. Pat. Nos. 4,968,312; 4,990,147; 5,062,840; and 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. Nos. 5,941,864; 5,977,430; and 6,013,063.

While some of the individual features of some of the embodiments of the present invention have been known in the art, even greater benefits in urinary toilet training than those previously seen are possible using the combinations of elements described herein. Additionally, using some of the related features described can lead to even greater synergistic benefits. For example, refastenable fasteners with easy open tabs and the sensory elements described with active graphics can provide an article which a child may easily apply, check, remove (including when urination is imminent) and provides multiple sensory based feedback signals (such as visible graphics, tactile sensation members, etc.). Such features re-enforce each other in ways previously not combined in the art.

As stated previously, the sensory element member of the present invention can provide a wetness signal, a temperature change signal, or a combination thereof. For example, a portion of the liquid absorbed by the wetness sensation member can partially evaporate thereby causing a cooling sensation for the wearer. The outer cover 62 of the absorbent article, may include a substantially vapor permeable material. The outer cover 62 is generally constructed to be permeable to at least water vapor and has a moisture vapor transmission rate of at least 1000 g/m$^2$/24 hr, preferably at least 2000 g/m$^2$/24 hr, more preferably at least 3000 g/m$^2$/24 hr., even more preferably at least 3500 g/m$^2$/24 hr, most preferably at least 4000 g/m$^2$/24 hr and even most preferably at least 4500 g/m$^2$/24 hr. For example, the outer cover 62 may define a moisture vapor transmission rate of from 1000 to 10000 g/m$^2$/24 hr or any value within the range. Materials which have a moisture vapor transmission rate less than those above may not allow a sufficient amount of air exchange and undesirably result in increased levels of humidity of the air inside the article during use. Some breathable backsheet materials are described in greater detail in PCT Application No. WO 95/16746; U.S. Pat. Nos. 5,938,648; 5,865,823; and 5,571,096. Other suitable exemplary materials and a suitable test method for measuring the MVTR is described in U.S. Pat. No. 6,448,467.

Measurement Methods

Temperature Change Response Measurement

Equipment

USB Data Acquisition System, OMB-DAQ-55 with Personal DAQView software from Omega Engineering Inc
 Thermocouples –K type thermocouple, with a 6" long, 0.020" diameter, stainless steel sheath, ending in a exposed junction. (Part Number—KMTSS-020E-6) from Omega Engineering Inc.
 Computer Suitable computer capable of running Personal DAQView Software.
 Saline 0.9% Saline heated to 37° C.±1° C.
 Syringe Capacity of at least 75 mL
 Timer Convenient Source, time measurements taken to nearest second
 Curved Plate A U-shaped Plexiglas plate to mount the test product on in a curved configuration. A suitable plate is 5 mm thick, Radius of Curvature of the U-portion is 250 mm, Height (upright walls from bottom of "U") is 160 mm, Width is 130 mm. The curved plate may be supported with side walls or other convenient mechanism to maintain upright, U-shaped disposition Test Procedure 1. Test fluid is 0.9% saline heated to 37° C.±1° C.
2. If the product is provided in a closed, pant-like form, open side seams of all products. If product contains defined side seams product should be opened at those locations. Otherwise, cut side panels with scissors at midpoint of side panels.
3. Mount the test product onto the curved plate. Any suitable mechanism may be used. Two sided adhesive strips or hook material with the hooks facing the inside of the "U" may be used for this purpose depending upon the surface properties of the outer cover of the test product. (An example of hook material is supplied by Velcro USA Inc., Manchester, N.H. 03108). Typical hook or adhesive mounting strip are 520 mm long and 10 mm to 30 mm wide. Each strip is placed parallel to, and between 30 mm and 40 mm away from, with a strip on either side of the longitudinal center line of the template. The hook strips allow the continuous attachment of the test product to the template. The product is attached to the template such that the topsheet is facing away from the template (i.e. toward the space defined by the inside of the "U"). Pant elastics should stay intact.
4. The thermocouples are affixed on the surface using strips of masking tape 5 to 6 mm in width and 20 to 40 mm long. The closest tape is positioned such that the thermocouple tip is exposed and the longitudinal edge of the tape strip is between 4 to 6 mm from the thermocouple tip. This tape is then used to attach the thermocouple on the surface to be measured such that the tip of the thermocouple is positioned no higher than 1 mm above said surface. More strips (generally less than 3) can be used to secure the remainder of the thermocouple.
5. Measure as follows to define the loading point
 a. (boy) 10.2 cm below front edge of the core, or
 b. (girl) 12.7 cm below front edge of the core.
 c. (unisex or generic) use boy product measurement for loading point
6. Draw 75 mls of 0.9 saline (heated to 37° C.±1° C.) into syringe.
7. Temperature measurement is started between 5 to 15 seconds before the introduction of fluid and continues for at least the next 600 seconds.
8. Using syringe, deposit the saline at the loading point with a constant rate of loading. Loading should be done over approximately 5 seconds or at approximately 15 mL/second.
9. Once fluid is deposited, start timer. Depositing of the fluid is considered to be the "urination event" for comparison of time with time parameters in the claims.
10. Data is collected via the OMB-DAQ-55 system and stored in the computer in a predetermined folder, in various forms. One common for is an ASCII text file which is easily exported to common spreadsheet software (Excel) for further analysis.
11. Using generated data determine $\Delta T$ (taking 37° C. as $T_o$) at 30 seconds from start of timer (urination event).
12. Using generated data determine cooling rates ($\Delta T$/second, taking 37° C. as $T_0$, and deposit of fluid as $t_0$) at the following intervals, 0 to 3 seconds, 3 to 10 seconds and 10 to 30 seconds from $T_0$.
13. Using generated data determine $T_{min}$ for 600 second interval. Determine $\Delta T_{max}$ defined as 37° C.$-T_{min}$. Duration of temperature change response is considered to be time at which thermocouple temperature is $T_{min}+$ 25% $\Delta T_{max}$.

Wetness Density Test

Purpose

This test simulates the introduction of urine into a training pant diaper. No pressure is applied while loading to simulate the baby urinating in a standing position.

Equipment

Template Flat Base unit on which to mount the test product
Filter Paper Ahlstrom Filtration Paper Code 632, 127×127 mm
Balance accuracy±0.01 g
Saline 0.9% Saline heated to 37° C.±1° C.
Graduated Cylinder Convenient Source
Timer Convenient Source, time measurements taken to nearest second
Weight Plastic Dimensions/Weight 127×127 mm, 297 grams
Metal Cylinder Metal Cylinder, Inside Diameter=60 mm, Outside Diameter=70 mm, Height=40 mm, Weight=327 grams.

Test Procedure

1. Test fluid is 0.9% saline heated to 37° C.±1° C.
2. If the product is provided in a closed, pant-like form, open side seams of all products. If product contains defined side seams product should be opened at those locations. Otherwise, cut side panels with scissors at midpoint of side panels.
3. Mount the test product with clamps onto a flat template in a flat stretched out condition to ensure no wrinkles in the topsheet or liners. The pant elastics should stay intact.
4. Weigh one piece of filter paper.
5. Measure as follows to define the loading point
 (boy) 10.2 cm below front edge of the core, or
 (girl) 12.7 cm below front edge of the core.
 (unisex or generic) use boy loading point measurement
6. Measure 75 mls of 0.9 saline (heated to 37° C.±1° C.) into the graduated cylinder.
7. Center the cylinder over the loading point and pour the saline from the graduated cylinder at the loading point. Loading should be done over approximately 5 seconds or at approximately 15 mL/second.
8. Once fluid is poured, start timer. Pouring the saline is considered to be the "urination event" for purposes of comparison of time with time parameters in the claims.

9. After 60 seconds have elapsed, place filter paper on the topsheet and then the plastic weight to ensure complete contact between the filter paper and the topsheet. The weight should be lowered slowly and applied gently to the filter paper.
10. After 10 seconds from weight application, lift the weight and filter paper off of the topsheet and weigh the filter paper.
11. Calculate wet weight minus dry filter paper weight in mg. This value is divided by 161.29 cm² to determine the wetness density in mg/cm².

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for wearing about the lower torso of a wearer said absorbent article comprising:
   a first waist region, a second waist region disposed opposite said first waist region, a crotch region connecting said first waist region and said second waist region,
   an outer cover, a water-permeable topsheet attached to said outer cover and having a body-facing surface;
   an absorbent core disposed between said outer cover and said topsheet; and
   a sensory element member at least partially disposed in said crotch region of said absorbent article, said sensory element member providing a feedback response to said wearer upon a urination event, said feedback response occurring within about 60 seconds of said urination event, said sensory element providing said feedback response for a duration of no longer than about 10 minutes beyond said urination event, said sensory element member comprising a body contacting portion; and
   wherein said feedback response provided by said sensory element member is selected from the group consisting of elements providing a tactile temperature change sensation, a tactile coolness sensation, and combinations thereof.

2. The absorbent article of claim 1 wherein said feedback response occurs within about 30 seconds of said urination event.

3. The absorbent article of claim 1 wherein said feedback response occurs within about 15 seconds of said urination event.

4. The absorbent article of claim 1 wherein said feedback response persists no longer than about 600 seconds.

5. The absorbent article of claim 1 wherein said feedback response persists no longer than about 300 seconds.

6. The absorbent article of claim 1 wherein said feedback response persists no longer than about 150 seconds.

7. The absorbent article of claim 1 wherein said body contacting portion has an area of at least about 50 cm².

8. The absorbent article of claim 1 wherein said body contacting portion has an area of at least about 100 cm².

9. The absorbent article of claim 1 wherein said body contacting portion has an area of at least about 200 cm².

10. The absorbent article of claim 1 wherein said body contacting portion of said sensory element member comprises a skin protecting feature selected from the group consisting of a pH buffer material, Zinc Oxide, enzyme inhibitors, skin care compositions and combinations thereof.

11. The absorbent article of claim 1 wherein said absorbent article is article is a disposable diaper.

12. The absorbent article of claim 1 wherein said absorbent article is a disposable pant-like garment.

13. The absorbent article of claim 12 wherein said disposable pant like garment comprises a refastenable fastening member.

14. The absorbent article of claim 13 wherein said refastenable fastening member comprises an adhesive or cohesive based fastening system.

15. The absorbent article of claim 13 wherein said refastenable fastening member comprises a tab and slot type mechanical fastener.

16. The absorbent article of claim 13 wherein said refastenable fastening member comprises a hook and loop type mechanical fastener.

17. The absorbent article of claim 13 wherein said disposable pant like garment comprises an easy open feature.

18. The absorbent article of claim 1 further comprising active graphics disposed on at least a portion of said article.

19. The absorbent article of claim 18 wherein said active graphics comprise at least one disappearing graphic.

20. The absorbent article of claim 18 wherein said active graphics comprise at least one appearing graphic.

21. The absorbent article of claim 1 wherein said outer cover comprises at least a portion which is water impermeable, breathable, and water vapor permeable.

22. The absorbent article of claim 1 further comprising a second sensory element member which provides an audible feedback response upon a urination event.

23. The absorbent article of claim 1 wherein said sensory element is at least partially separable from said topsheet.

24. The absorbent article of claim 1 wherein said sensory element member is elastically foreshortened along at least a portion of the length of said topsheet.

25. The absorbent article of claim 1 wherein said body contacting portion of said sensory element includes a wearer facing surface and wherein the wearer facing surface of the body contacting portion of said sensory element includes an adhesive to promote contact between the wearer facing surface and said wearer.

26. The absorbent article of claim 1 further comprising a pair of barrier leg cuffs wherein said sensory element member is connected with said barrier leg cuffs.

27. The absorbent article of claim 1, wherein said body contacting portion of said sensory element member has an area of at least about 25 cm².

28. An absorbent article for wearing about the lower torso of a wearer said absorbent article comprising:
   a front waist region, a rear waist region disposed opposite said front waist region, a crotch region connecting said front waist region and said rear waist region,
   an outer cover, a water-permeable topsheet attached to said outer cover and having a body-facing surface;

an absorbent core disposed between said outer cover and said topsheet; and a temperature change member at least partially disposed in said crotch region of said absorbent article, said temperature change member providing a tactile temperature change sensation to said wearer upon a urination event, said tactile temperature change sensation occurring within about 30 seconds of said urination event, said tactile temperature change sensation persisting no longer than about 300 seconds beyond said urination event, said temperature change member providing surface temperature change of from about 5° C. to about 20° C. at 30 seconds after said urination event.

29. The absorbent article of claim 28 wherein said tactile temperature change sensation occurs within about 15 seconds of said urination event.

30. The absorbent article of claim 29 wherein said tactile temperature change sensation occurs within about 10 seconds of said urination event.

31. The absorbent article of claim 28 wherein said tactile temperature change sensation persists no longer than about 150 seconds.

32. The absorbent article of claim 28 wherein said temperature change member comprises body contacting portion said body contacting portion having an area of at least about 25 cm².

33. The absorbent article of claim 32 wherein said body contacting portion has an area of at least about 100 cm².

34. The absorbent article of claim 28 wherein said absorbent article is a disposable pant-like garment.

35. The absorbent article of claim 34 wherein said disposable pant like garment comprises a refastenable fastening member.

36. The absorbent article of claim 34 wherein said disposable pant like garment comprises an easy open feature.

37. The absorbent article of claim 28 further comprising active graphics disposed on at least a portion of said article.

38. The absorbent article of claim 28 wherein said outer cover comprises a portion which is water impermeable, breathable and water vapor permeable.

39. An absorbent article for wearing about the lower torso of a wearer said absorbent article comprising:

a front waist region, a rear waist region disposed opposite said front waist region, a crotch region connecting said front waist region and said rear waist region, an outer cover, a water-permeable topsheet attached to said outer cover and having a body-facing surface;

an absorbent core disposed between said outer cover and said topsheet; and a temperature change member at least partially disposed in said crotch region of said absorbent article, said temperature change member providing a tactile temperature change sensation to said wearer upon a urination event, said temperature change member providing a temperature change occurring at a rate of at least 1° C./sec at some point during the first 2 minutes following said urination event.

40. The absorbent article of claim 39 wherein said temperature change occurs at a rate of at least 2° C./sec within the first 20 seconds following said urination event.

41. The absorbent article of claim 39 wherein said temperature change occurs at a rate of at least 2° C./sec within the first 5 seconds following said urination event.

42. The absorbent article of claim 40 wherein said temperature change occurs at a rate of at least 3° C./sec within the first 20 seconds following said urination event.

43. The absorbent article of claim 41 wherein said temperature change occurs at a rate of at least 3° C./sec within the first 5 seconds following said urination event.

44. The absorbent article of claim 41 wherein said temperature change occurs at a rate of at least 5° C./sec within the first 20 seconds following said urination event.

45. The absorbent article of claim 43 wherein said temperature change occurs at a rate of at least 5° C./sec within the first 5 seconds following said urination event.

* * * * *